US010166231B2

(12) United States Patent
Inghelbrecht et al.

(10) Patent No.: US 10,166,231 B2
(45) Date of Patent: Jan. 1, 2019

(54) FREEZE DRIED DRUG NANOSUSPENSIONS

(71) Applicant: Janssen Pharmaceutica NV, Beerse (BE)

(72) Inventors: Sabine Karine Katrien Inghelbrecht, Beerse (BE); Jakob Andreas Beirowski, Erlangen (DE); Henning Gieseler, Erlangen (DE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/204,587

(22) Filed: Jul. 7, 2016

(65) Prior Publication Data

US 2016/0317534 A1     Nov. 3, 2016

Related U.S. Application Data

(63) Continuation of application No. 14/111,689, filed as application No. PCT/EP2012/056818 on Apr. 13, 2012.

(60) Provisional application No. 61/475,811, filed on Apr. 15, 2011.

(51) Int. Cl.
| | | |
|---|---|---|
| *A01N 43/54* | (2006.01) | |
| *A61K 31/505* | (2006.01) | |
| *A61K 9/19* | (2006.01) | |
| *A61K 9/51* | (2006.01) | |
| *A61K 47/32* | (2006.01) | |
| *A61K 9/00* | (2006.01) | |
| *A61K 9/16* | (2006.01) | |

(52) U.S. Cl.
CPC .......... *A61K 31/505* (2013.01); *A61K 9/0019* (2013.01); *A61K 9/1635* (2013.01); *A61K 9/1641* (2013.01); *A61K 9/19* (2013.01); *A61K 9/51* (2013.01); *A61K 47/32* (2013.01)

(58) Field of Classification Search
CPC ............ A61K 31/4155; A61K 2300/00; A61K 9/0014; A61K 45/06; A61K 9/0019; A61K 9/0053; A61K 9/06; A61K 9/2054; A61K 9/4858; A61K /
See application file for complete search history.

(56) References Cited

U.S. PATENT DOCUMENTS

| | | | |
|---|---|---|---|
| 6,284,277 B1 | 9/2001 | Bouloumie et al. | |
| 2010/0003332 A1 | 1/2010 | Bae | |

FOREIGN PATENT DOCUMENTS

| | | |
|---|---|---|
| CN | 1012-83982 A | 10/2008 |
| CN | 1014-78950 A | 7/2009 |
| CN | 1016-12131 A | 12/2009 |
| CN | 1019-04820 A | 12/2010 |
| CN | 1019-53808 A | 1/2011 |
| EP | 0499-299 A2 | 8/1992 |
| JP | 2008-538751 A | 11/2008 |
| JP | 2009-518306 A | 5/2009 |
| JP | 2009-541271 A | 11/2009 |
| JP | 2010-533148 A | 10/2010 |
| RU | 2163801 C2 | 3/2001 |
| RU | 2331424 C2 | 2/2006 |
| WO | WO2004/050058 A2 | 6/2004 |
| WO | WO 2004/054549 A1 | 7/2004 |
| WO | WO 2006/109183 A1 | 10/2006 |
| WO | WO 2007/147882 | 12/2007 |
| WO | WO2007/147882 A2 | 12/2007 |
| WO | WO 2008/051245 A2 | 5/2008 |
| WO | WO2008/110619 A1 | 9/2008 |
| WO | WO2009/007441 A1 | 1/2009 |
| WO | WO 2009/007441 A2 | 1/2009 |

OTHER PUBLICATIONS

Deng et al. "Advances for Parenteral Delivery of Slightly Water-Soluble Drugs" Chinese Journal of Pharmaceuticals 2010 vol. 41(11) pp. 856-862.
Pikal M J. 2002. Freeze Drying, In: J. Swarbrick (Ed.), Encyclopedia of Pharmaceutical Technology, Vol. 2, Marcel Dekker, New York (2002) 1299-1326).
Rabinow B Nanosuspensions for Parenteral Delivery 2007 p. 33-49.
Schwarz et al "Freeze-Drying of Drug-Free and Drug-Loaded Solid Lipid Nanoparticles (SLN)" Int. Journal of Pharmaceutics 1997 vol. 157 pp. 171-179.
International Search Report and Written Opinion dated Jul. 2, 2012, for Corresponding International Application PCT/EP2012/056818.
Nakarani et al "Itraconazole Nanosuspension for Oral Delivery: Formulation, Characterization and In Vitro Comparison With Marketed Formulation" Daru: Journal of Faculty of Pharmacy, Tehran University of Medical Sciences, 2010, vol. 18(2) pp. 84-90.
Pornanong "In Vitro Plasma Compatibility Study of a Nanosuspension Formulation" PDA Journal of Pharmaceutical Science and Technology 2006 vol. 60(4) pp. 211-217.
Van'T Klooster et al "Pharmacokinetics and Disposition of Rilpivirine (TMC278) Nanosuspension As a Long-Acting Injectable Aniretroviral Formulation" Antimicrobial Agents and Chemotherapy 2010 vol. 54(5) pp. 2042-2050.
Thassu et al Nanoparticulate Drug Delivery System ((USA) Translated by Jiancheng Wang, Qiangyi Zhang, Peking University Medical Press, Jul. 2010.
Wang et al "Molecular Dynamics Simulations in Pharmaceutics" Chinese Journal of Pharmaceuticals 2010 vol. 41(11) p. 863.
Merisko-Liversridge, et al., "Nanosizing: a formulation approach for poorly-water-soluble compounds," European Journal of Pharmaceutical Sciences, 18: 113-120 (2003).

(Continued)

*Primary Examiner* — Jean P Cornet

(57) ABSTRACT

The present invention relates to a freeze-dried (also called lyophilized) drug nanosuspension. The present freeze-dried drug nanosuspension composition has an acceptable stability of the particle size distribution during storage, including long term storage.

11 Claims, 6 Drawing Sheets

(56) References Cited

OTHER PUBLICATIONS

Figure 1:
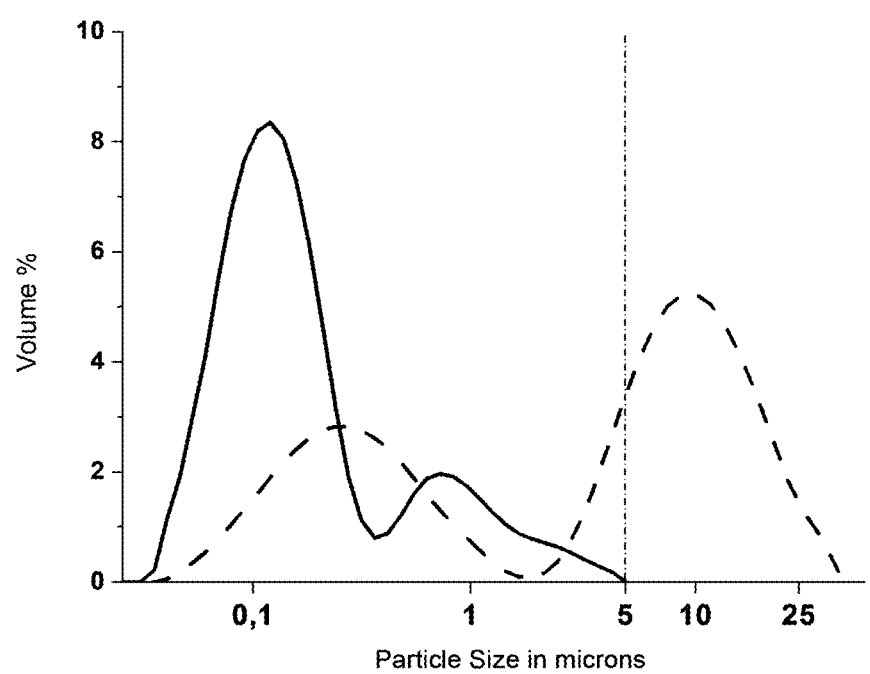

Müller, et al., "Nanosuspensions as particulate drug formulations in therapy Rationale for development and what we can expect for the future," Advanced Drug Delivery Reviews, 47: 3-19 (2001).
Kocbek et ai, I nternational Journal of Pharmaceutics 312 (2006) 179-186.
Baert et ai, European Journal of Pharmaceutics and Biopharmaceutics 72 (2009) 502-508.
Abdelwahed et ai, Advanced Drug Delivery Reviews 58 (2006) 1688-1713.
Lee, M. K. et al. Cryoprotectants for Freeze Drying of Drug Nano-Suspensions: Effect of Freezing Rate, J. Pharmaceutical Sci. vol. 98, No. 12, 4808-4816, 4812 (2009).
Schwarz, C. et al. Freeze-drying of drug-free and drug-loaded solid lipid nanoparticles (SLN), Int'l J. Pharmaceutics 157 (1997) 171-179, 173-176.
Lee, J. et al. Critical freezing rate in freeze drying nanocrystal dispersions, J. Controlled Release 111 (2006) 185-192.
Beirowski, Jakob et al., "Freeze-Drying of Nanosuspensions, 1: Freezing Rate Versus Formulation Design as Critical Factors to Preserve the Original Particle Size Distribution", Journal of Pharmaceutical Sciences, vol. 100, No. 5, May 2011, pp. 1958-68.
Beirowski, Jakob et al., "Freeze Drying of Nanosuspensions, 2: the Role of the Critical Formulation Temperature on Stability of Drug Nanosuspensions and Its Practical Implication on Process Design", Journal of Pharmaceutical Sciences, vol. 100, No. 10, Oct. 2011, pp. 4471-81.
Beirowski, Jakob et al., "Freeze-Drying of Nanosuspensions, Part 3: Investigation of Factors Compromising Storage Stability of Highly Concentrated Drug Nanosuspensions", Journal of Pharmaceutical Sciences, vol. 101, No. 1, Jan. 2012, pp. 354-362.

FREEZE DRIED DRUG NANOSUSPENSIONS

CROSS REFERENCE TO RELATED APPLICATIONS

This application is a continuation of U.S. patent application Ser. No. 14/111,689, filed on Oct. 14, 2013, which is a national phase entry of International Application No. PCT/EP2012/056818, filed on Apr. 13, 2012, which claims the benefit of U.S. Provisional Application No. 61/475,811, filed on Apr. 15, 2011, the entire contents of which are incorporated herein by reference in their entireties.

The present invention relates to a freeze-dried (also called lyophilized) drug nanosuspension. The present freeze-dried drug nanosuspension composition has an acceptable stability of the particle size distribution during storage, including long term storage. Long term storage stability of particle size distribution includes stability for a period of 2 weeks, in particular a period of one month, more in particular a period of two months, even more in particular a period of 3 months or a period of 6 months or a period of at least 6 months up to 2 years. Long term storage stability of particle size distribution is an important property because it is an integral part of every formulation development procedure.

Nanoparticles or nanosuspensions are known in the prior art, having been described, for example, in EP-A-0 499 299.

The drug nanosuspension formulation which is the precursor formulation for the freeze-dried drug nanosuspension formulation of the present invention is a liquid formulation wherein the drug is suspended in the form of nanoparticles. The liquid or dispersion medium is preferably an aqueous medium, such as water.

The drug nanosuspension precursor formulation typically comprises a steric stabilizer, preferably a surfactant (e.g. a polymeric surfactant) or a polymer. The steric stabilizer is adsorbed or attached onto the surface of the drug nanoparticles and provides a large and dense steric barrier which overcomes attractive van der Waals forces and hence the steric stabilizer reduces aggregation, agglomeration or even particle fusion. This technique allows remarkable high dose loadings of the nanosuspension (e.g. up to 400 mg of drug/mL). The steric stabilizers are preferably excipients which are pharmaceutically acceptable.

The drug nanoparticles have typically a mean particle size below 1 μm and a $d^{99}$-value of less than 5 μm. More in particular, the $d^{95}$-value is 0.9 μm. (d99 is X or d95 is X means that 99% or 95% of the particles by weight (or by other suitable measurement techniques such as by volume or number) are below that size X).

In particular, the average particle size of the nanoparticles of the nanosuspensions to be freeze dried or the nanosuspension resulting from reconstitution of the freeze-dried drug nanosuspension may be below about 1000 nm, or below about 500 nm, or below about 400 nm, or below about 300 nm, or below about 200 nm. Preferably, the average particle size is about 200 nm or about 400 nm or about 800 nm, more preferably about 200 nm.

A possible approach to produce a drug-nanosuspension is comminution of the drug substance in a stirred media mill by wet bead milling.

Drug nanosuspensions can improve solubility, dissolution rate, bioavailability. Drug nanosuspensions can also be used as sustained or delayed release (depot) formulation. Such formulations can be used for long term treatment or long term prevention, for instance when administered parenterally, e.g. intramuscularly or subcutaneously. This means that the formulation is able to provide effective plasma levels—plasma levels above a minimal therapeutical concentration—for a certain period, such as for at least 1 week, or at least two weeks, or at least 1 month or at least two months or at least three months. The formulation is also able to provide plasma level which are below a side-effect producing threshold value. The threshold value is the mean plasma level during a considerable period of time, e.g. for more than 15 minutes depending on the actual drug, above which patients may experience undesirable side effects, or conversely, the value of the plasma level under which the systemic tolerance of the formulation in question is still acceptable. The threshold value does not hold for transient, high plasma levels during a short period of time, e.g. for less than 15 minutes depending on the actual drug, which are due, for example to unexpected burst-release of the active ingredient.

Both of the foregoing features—plasma levels above a minimal therapeutical concentration but below a side-effect producing threshold value—are considered to be basic requirements that a contemporary depot formulation should fulfil in order to be acceptable for the intended patients. Limiting the number of drug administrations and the occurrence of undesirable side effects after each administration will undoubtedly improve the patients' compliance with the therapy. However, beyond these basic requirements, a number of further desiderata can be identified which would further improve patients' compliance, the two most notable being good local tolerance and ease of administration.

For injectables, good local tolerance means minimal irritation and inflammation at the site of injection; ease of administration refers to the size of needle and length of time required to administer a dose of a particular drug formulation.

A significant drawback of a liquid drug-nanosuspension is its limited long term stability. Settling and Ostwald-ripening effects are frequently recognized instability issues.

Therefore, freeze-dried drug nanosuspensions may be an appealing alternative. In this way, the shelf life of the formulation with the drug in nanoparticle range may be increased. Preferably, the freeze-dried drug nanosuspension itself has an acceptable long term stability, especially in relation with the average particle size or the particle size distribution. After storage and upon reconstitution of the freeze-dried drug nanosuspension, the average particle size, the particle size distribution, the $d^{50}$, $d^{90}$, $d^{95}$ or $d^{99}$ is preserved or is still acceptable.

These freeze-dried drug nanosuspensions may be reconstituted ex tempore to a liquid nanosuspension which can then be administered. Administration of said reconstituted nanosuspension includes oral administration or parenteral administration, such as for example intravenous, intramuscular or subcutaneous administration. Administration is preferably parenteral administration such as for example intramuscular or subcutaneous administration. Care has to be taken that the reconstituted suspension stays evenly dispersed or that it is easily dispersable upon shaking enabling homogenous administration.

FIGURES

FIG. 1.: Comparison of the particle size distributions of a drug stock-nanosuspension stabilized with 50 mg/mL Cremophor EL directly after freeze-drying and at 3 months of storage at ambient conditions (dashed line). The 5 μm boundary represents the upper particle size limit for a parenteral drug-nanosuspension.

Figure 2:
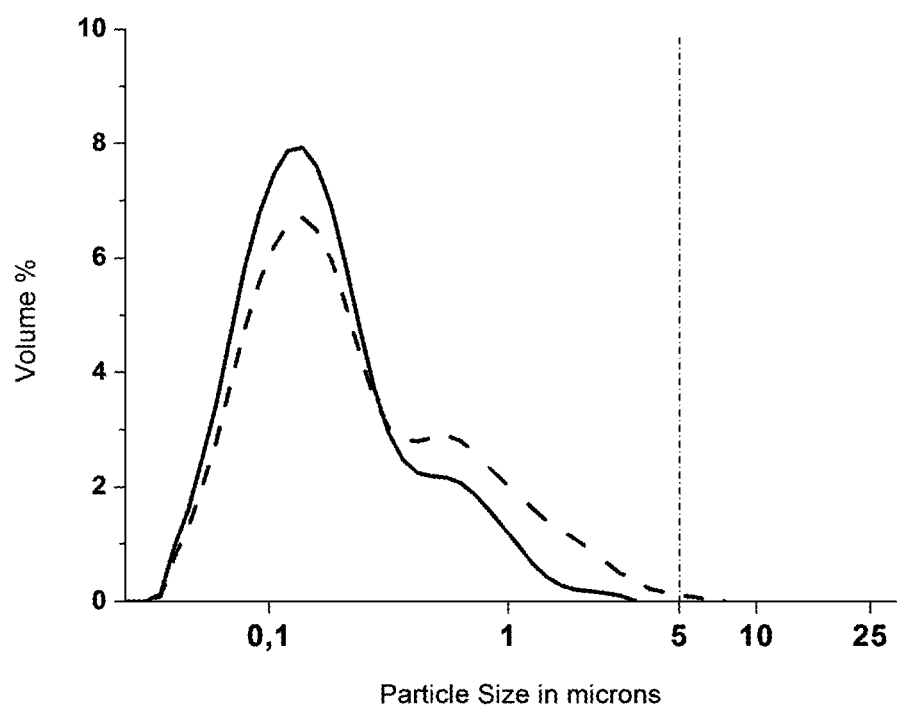

FIG. 2.: Comparison of the particle size distributions of a rilpivirine stock-nanosuspension stabilized with 50 mg/mL Poloxamer 338 directly after freeze-drying and at 3 months of storage at ambient conditions (dashed line).

Figure 3:
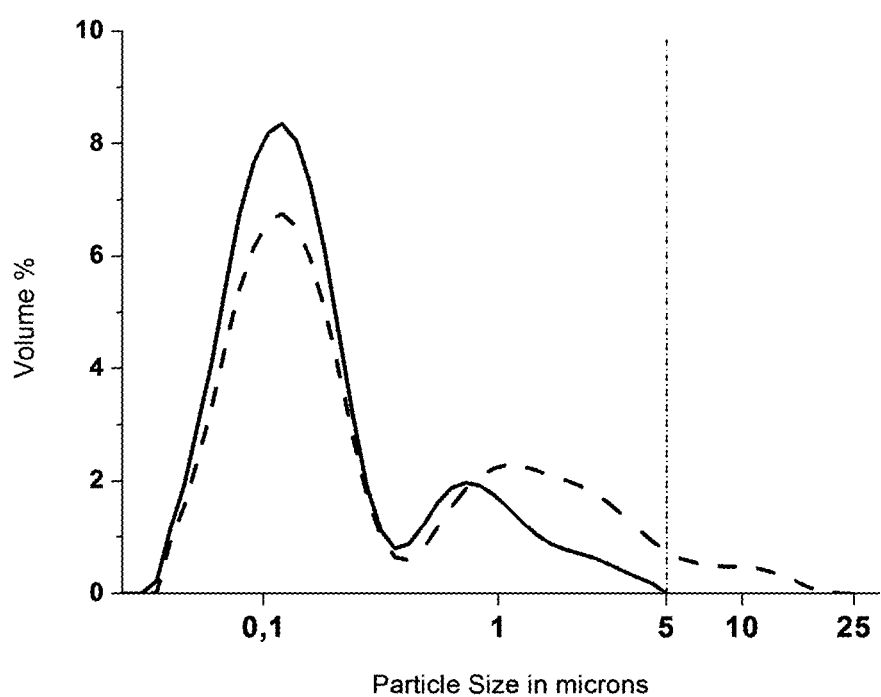

FIG. 3.: Comparison of the particle size distributions of a drug stock-nanosuspension stabilized with 50 mg/mL Cremophor EL after aggressive freeze-drying process conditions (solid line, shelf temperature during primary drying was after freezing directly increased to 40° C.) and conservative freeze-drying process conditions (dashed line, shelf temperature 0° C.). Note that during both runs product temperatures were measured well above the CFT (critical formulation temperature, which is denoted as the glass transition temperature of the maximum freeze concentrated solute Tg', typically evaluated by differential scanning calorimetry (DSC) (Pikal M J. 2002. Freeze drying, in: J. Swarbrick (Ed.), Encyclopedia of Pharmaceutical Technology, vol. 2, Marcel Dekker, New York (2002) 1299-1326).

Figure 4:
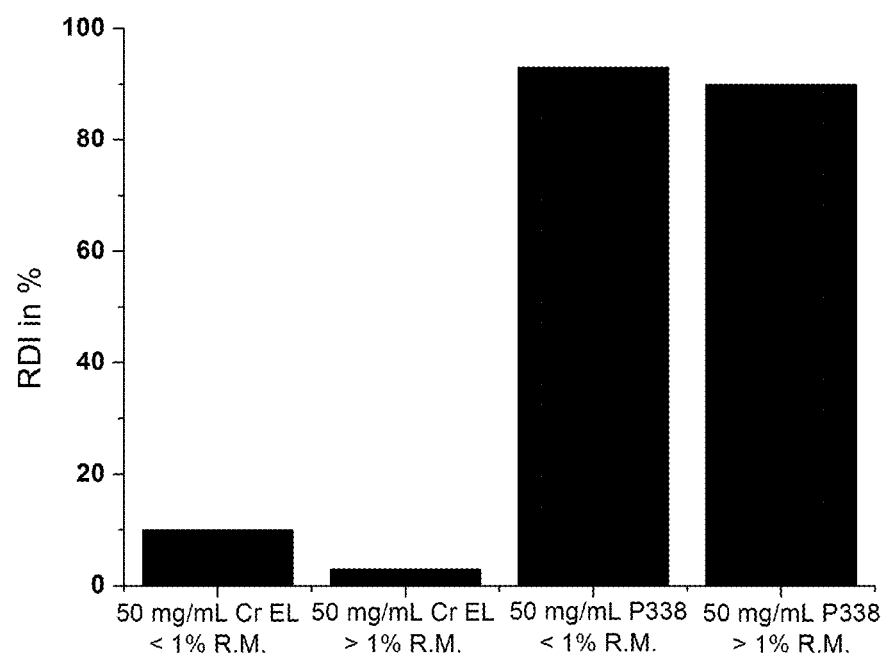

FIG. 4.: Comparison of the redispersibility indices (RDI) for a drug stock-nanosuspensions after 3 months of storage at ambient conditions stabilized with either Cremophor EL (Cr EL) or Poloxamer 338 (P338) as a function of a high or low residual moisture content (R.M.).

Figure 5:
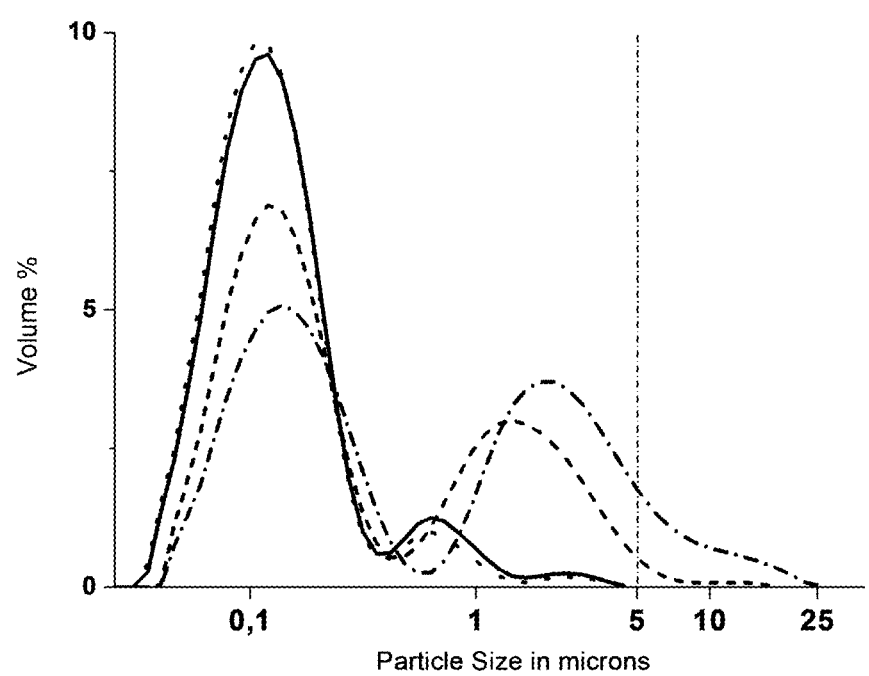

FIG. 5.: Comparison of the particle size distributions of a drug-nanosuspension stabilized with 50 mg/mL Cremophor EL and 50 mg/mL trehalose as a lyoprotectant directly after freeze-drying and at 3 months of storage at ambient conditions as a function of a high or low residual moisture content. Note that initial nanoparticle stability was independent of the water content (solid versus dotted line) but after storage residual moisture content below 1% (dashed line) revealed better particle stability compared to a water content above 1% (dashed-dotted line).

Figure 6:
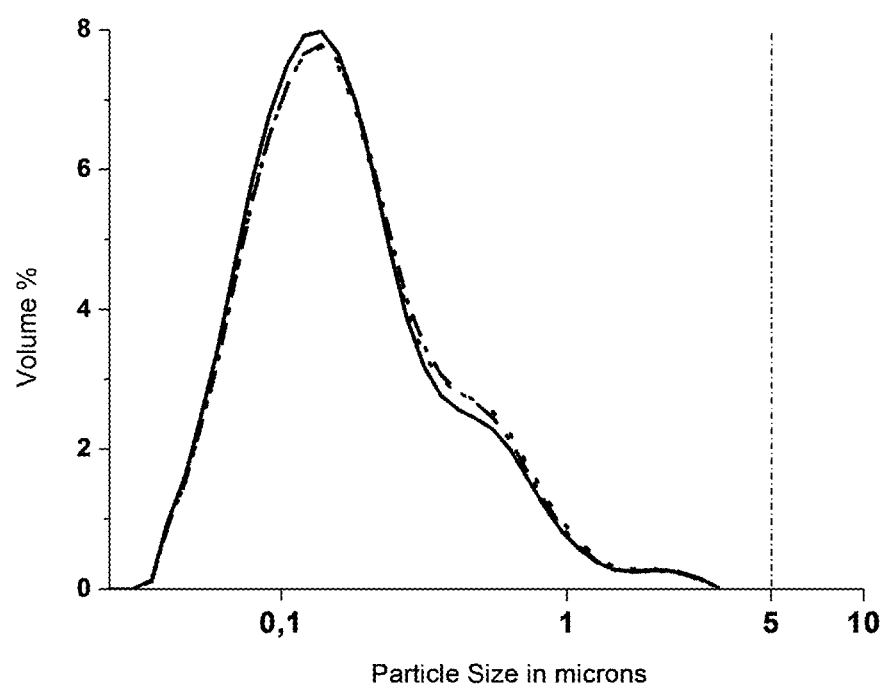

FIG. 6.: Comparison of the particle size distributions of a highly concentrated drug-nanosuspension (200 mg/mL rilpivirine) stabilized with 50 mg/mL Poloxamer 338 and 50 mg/mL PVP K15 as a lyoprotectant showing that the original particle size distribution after freeze-drying (solid line) was completely preserved after 3 months of storage at 25° C. (dashed line) as well as at 40° C. (dotted line).

DESCRIPTION OF THE INVENTION

Hence, the present invention relates to a freeze-dried drug nanosuspension, meaning a freeze-dried nanosuspension comprising a drug or an aqueous nanosuspension comprising a drug and being freeze-dried to a solid composition.

Suitable drugs or active pharmaceutical ingredients that can be used in the freeze-dried nanosuspensions of the present invention include, without limitation:
  analgesic and anti-inflammatory drugs (NSAIDs, fentanyl, indomethacin, ibuprofen, ketoprofen, nabumetone, paracetamol, piroxicam, tramadol, COX-2 inhibitors such as celecoxib and rofecoxib);
  anti-arrhythmic drugs (procainamide, quinidine, verapamil);
  antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, norfloxacin, ofloxacin, oxacillin, phenoxymethylpenicillin potassium, pyrimethamine-sulfadoxime, streptomycin);
  anti-coagulants (warfarin);
  antidepressants (amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one);
  anti-diabetic drugs (glibenclamide, metformin);
  anti-epileptic drugs (carbamazepine, clonazepam, ethosuximide, gabapentin, lamotrigine, levetiracetam, phenobarbitone, phenytoin, primidone, tiagabine, topiramate, valpromide, vigabatrin);
  antifungal agents (amphotericin, clotrimazole, econazole, fluconazole, flucytosine, griseofulvin, itraconazole, ketoconazole, miconazole nitrate, nystatin, terbinafine, voriconazole);
  antihistamines (astemizole, cinnarizine, cyproheptadine, decarboethoxyloratadine, fexofenadine, flunarizine, levocabastine, loratadine, norastemizole, oxatomide, promethazine, terfenadine);
  anti-hypertensive drugs (captopril, enalapril, ketanserin, lisinopril, minoxidil, prazosin, ramipril, reserpine, terazosin);
  anti-muscarinic agents (atropine sulphate, hyoscine);
  antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics, such as daunorubicin, doxorubicin, idarubicin, epirubicin, bleomycin, dactinomycin, mitomycin; HER 2antibody, such as trastuzumab; podophyllotoxin derivatives, such as etoposide, teniposide; farnesyl transferase inhibitors; anthrachinon derivatives, such as mitoxantron; abiraterone or an ester thereof such as abiraterone acetate);
  anti-migraine drugs (alniditan, naratriptan, sumatriptan);
  anti-Parkinsonian drugs (bromocriptine mesylate, levodopa, selegiline);
  antipsychotic, hypnotic and sedating agents (alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem);
  anti-stroke agents (lubeluzole, lubeluzole oxide, riluzole, aptiganel, eliprodil, remacemide);
  antitussive (dextromethorphan, laevodropropizine);
  antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea, etravirine, dapivirine, rilpivirine, darunavir, tenofovir or tenofovir disoproxil fumarate, emtricitabine);

beta-adrenoceptor blocking agents (atenolol, carvedilol, metoprolol, nebivolol, propanolol);

cardiac inotropic agents (amrinone, digitoxin, digoxin, milrinone);

corticosteroids (beclomethasone dipropionate, betamethasone, budesonide, dexamethasone, hydrocortisone, methylprednisolone, prednisolone, prednisone, triamcinolone);

disinfectants (chlorhexidine);

diuretics (acetazolamide, frusemide, hydrochlorothiazide, isosorbide);

essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme);

gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine);

haemostatics (aminocaproic acid);

lipid regulating agents (atorvastatin, lovastatin, pravastatin, probucol, simvastatin);

local anaesthetics (benzocaine, lignocaine);

opioid analgesics (buprenorphine, codeine, dextromoramide, dihydrocodeine, hydrocodone, oxycodone, morphine);

parasympathomimetics and anti-dementia drugs (AIT-082, eptastigmine, galanthamine, metrifonate, milameline, neostigmine, physostigmine, tacrine, donepezil, rivastigmine, sabcomeline, talsaclidine, xanomeline, memantine, lazabemide);

sex hormones (oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate);

stimulating agents (sildenafil);

vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate);

including their stereochemically isomeric forms;

the N-oxides thereof, the pharmaceutically acceptable acid or base addition salts thereof or the solvates thereof.

Pharmaceutically acceptable acid addition salts comprise the acid addition salt forms which can conveniently be obtained by treating the base form of the active ingredient with appropriate organic and anorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxy-propanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Active ingredients containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term solvates comprises the hydrates and solvent addition forms which the active ingredients or the pharmaceutically acceptable salts thereof, are able to form. Examples of such forms are e.g. hydrates, alcoholates and the like.

The N-oxide forms of the active ingredients comprise those active ingredients wherein one or several tertiary nitrogen atoms are oxidized to the so-called N-oxide.

The term "stereochemically isomeric forms" defines all the possible stereoisomeric forms which the active ingredients may possess. More in particular, stereogenic centers may have the R- or S-configuration, and active ingredients containing one or more double bonds may have the E- or Z-configuration.

In one embodiment, the drug or active pharmaceutical ingredient is an antifungal, such as for example itraconazole, or an antiviral, in particular an anti-HIV agent, more in particular a non nucleoside reverse transcriptase inhibitor (NNRTI), such as for example dapivirine, etravirine or rilpivirine.

The concentration of the drug in the nanosuspension to be freeze dried may range between 1 and 500 mg/ml or between 1 and 400 mg/ml or between 50 and 200 mg/ml or between 50 and 100 mg/ml or between 10 and 100 mg/ml or between 10 and 75 mg/ml or between 10 and 50 mg/ml or between 20 and 50 mg/ml or is about 200 mg/ml or is about 300 mg/ml.

A high nanoparticle concentration improves the mechanical stability of the freeze-dried cake.

The freeze-dried drug nanosuspension may be reconstituted to a liquid drug nanosuspesnion with the same drug concentration as in the nanosuspension which was freeze-dried or with a different drug concentration (more or less concentrated).

In one embodiment, the present invention relates to a freeze-dried drug nanosuspension wherein the drug is slightly soluble, very slightly soluble or practically insoluble according to USP 33, general notes, 5. Monograph components. In particular, the slightly soluble, very slightly soluble or practically insoluble drug is selected from the slightly soluble, very slightly soluble or practically insoluble drugs listed in the above list. Preferred drugs are selected from itraconazole, etravirine, dapivirine, rilpivirine. The drug is preferably a small chemical molecule active pharmaceutical ingredient (different from a large molecule such as for example a peptide or protein or DNA/RNA sequence).

In one embodiment, the present invention relates to a freeze-dried nanosuspension comprising a drug, in particular a slightly soluble, very slightly soluble or practically insoluble drug, and further comprising a steric stabilizer. In one embodiment, the steric stabilizer is a solid at room temperature.

In one embodiment, the steric stabilizer is a crystalline solid at room temperature, in particular the steric stabilizer is a crystalline solid at room temperature and has a melting point equal to or above 30° C. or a melting point equal to or above 50° C. or a melting point equal to or above 75° C. or a melting point equal to or above 90° C. In one embodiment, the steric stabilizer is an amorphous solid at room temperature, in particular the steric stabilizer is an amorphous solid at room temperature and has a glass transition temperature (Tg) equal to or above 30° C. or a Tg equal to or above 50° C. or a Tg equal to are above 75° C. or a Tg equal to or above 90° C.

The steric stabilizer provides an acceptable stability of the particle size distribution during storage, including long term storage, of the freeze-dried drug nanosuspension. It was found that the freezing rate is not a critical factor to preserve the original particle size distribution of the nanoparticles in the freeze-dried drug nanosuspension.

Determination of particle size distribution stability of the freeze-dried drug nanosuspension can be done by calculating the re-dispersibility index (RDI) or by determining the $d^{50}$ or $d^{90}$ or $d^{99}$ values directly after freeze drying (T0) and after the storage period, for example after 1 or 2 or 3 months of storage (T1, T2, T3). The RDI is defined as $D_0/D$ where $D_0$ is the volume weighed mean particle size after freeze-drying at $T_0$ and D is the corresponding value after the storage period for instance after 3 months of storage. A RDI of 100% would therefore mean that the stored freeze-dried drug-nanosuspension can be completely transformed to the original particle size at $T_0$ after rehydration. A freeze dried drug nanosuspension has an acceptable particle size storage stability if the RDI after 3 months at 25° C. is at least 90%, in particular at least 92% or 94% or 96% or 98%. In particular a freeze dried drug nanosuspension has an acceptable particle size storage stability if the RDI after 3 months at 40° C. is at least 90%, in particular at least 92% or 94% or 96% or 98%.

In one embodiment, the steric stabilizer is a solid, crystalline or amorphous, at room temperature and is a polymer or a surfactant (e.g. a polymeric surfactant). In a preferred embodiment, the steric stabilizer is poloxamer 338, especially in freeze-dried nanosuspensions for parenteral formulations. In a preferred embodiment, the steric stabilizer is hydroxypropyl methylcellulose, especially in freeze-dried nanosuspensions for oral administration.

The concentration of the steric stabilizer in the nanosuspension to be freeze dried may range between 1 and 200 mg/ml or between 10 and 100 mg/ml or between 10 and 75 mg/ml or between 10 and 50 mg/ml or between 20 and 50 mg/ml or is about 33.3 mg/ml or about 50 mg/ml.

In one embodiment, the present invention relates to a freeze-dried drug nanosuspension comprising a steric stabilizer as described in any of the above embodiments, and further comprising a cryoprotectant or a lyoprotectant. A cryoprotectant is a compound that stabilizes the components to be freeze-dried during the freezing step. A lyoprotectant is a compound that stabilizes the components to be freeze-dried during the dehydration step. Many excipients can serve as both cryoprotectants and lyoprotectants.

In one embodiment the cryoprotectant or lyoprotectant is a saccharide, in particular a mono- or disaccharide. such as for example sucrose, trehalose, mannitol.

In one embodiment, the cryoprotectant or lyoprotectant is a polymer, such as for example polyvinyl pyrrolidone, e.g. PVP K12, PVP K15 or PVP K17, PVP K15 and PVP K17 being preferred.

In one embodiment the cryoprotectant or lyoprotectant is a mixture of a saccharide and a polymer, e.g. a mixture of PVP and trehalose.

The cryoprotectant or lyoprotectant may further improve the stability of the particle size distribution during storage, including long term storage, of the freeze-dried drug nanosuspension.

The concentration of the cryoprotectant or lyoprotectant in the nanosuspension to be freeze dried may range between 1 and 200 mg/ml or between 10 and 100 mg/ml or between 10 and 75 mg/ml or between 10 and 50 mg/ml or between 20 and 50 mg/ml or is about 12.5 mg/ml or about 25 mg/ml or about 50 mg/ml or about 75 mg/ml.

In a preferred embodiment, the lyoprotectant or cryoprotectant concentration is as low as possible to prevent shrinkage or collapse of the freeze-dried cake but sufficiently high to assure stabilization of the nanoparticles and the concentration of the steric stabilizer is a minimum concentration which is typically higher than the minimum concentration to achieve initial nanoparticle stability right after milling to obtain the nanosuspension.

In one embodiment the freeze-dried drug nanosuspension as described in any of the above embodiments has a residual moisture content equal to or below 2% w/w or equal to or below 1% w/w or equal to or below 0.5% w/w. This limited residual moisture content further improves the stability of the particle size distribution during storage, including long term storage, of the freeze-dried nanosuspension.

In one embodiment, the present invention relates to a freeze-dried drug nanosuspension as described in any of the above embodiments for use in the preparation of a medicament, in particular a liquid drug nanosuspension, more in particular an aqueous drug nanosuspension for oral or parenteral administration, in particular parenteral administration, more in particular subcutaneous or intramuscular administration.

The present invention also relates to an aqueous nanosuspension obtained by reconstituting a freeze-dried drug nanosuspension as described hereinabove or hereinafter with a liquid or dispersion medium, in particular an aqueous dispersion medium, for example water or water for injection.

The present invention also relates to a process for preparing a liquid nanosuspension, in particular an aqueous nanosuspension, characterized by reconstituting the freeze-dried drug nanosuspension as described hereinabove or hereinafter with a liquid or dispersion medium, in particular with an aqueous dispersion medium.

The freeze-dried drug nanosuspension of the present invention may also further comprise pharmaceutically acceptable ingredients. The latter comprise any ingredients for use in injectable formulations or in suspension formulations or in oral formulations. These ingredients may be selected from one or more of a suspending agent, a buffer, a pH adjusting agent, a preservative, an isotonizing agent, and the like ingredients. In one embodiment, said ingredients are selected from one or more of a suspending agent, a buffer, a pH adjusting agent, and optionally, a preservative and an isotonizing agent. Particular ingredients may function as two or more of these agents simultaneously, e.g.

behave like a preservative and a buffer, or behave like a buffer and an isotonizing agent.

Examples of pharmaceutically acceptable ingredients are described further below.

In one embodiment, the present invention relates to a freeze-dried nanosuspension as described in any of the above embodiments wherein the drug is an anti HIV drug, in particular a non nucleoside reverse transcriptase inhibitor (NNRTI) such as for example dapivirine, etravirine or rilpivirine, in particular rilpivirine. Said nanosuspension may be for use in the preparation of a medicament, in particular a liquid nanosuspension of the anti HIV agent, more in particular an aqueous nanosuspension of the anti HIV drug for parenteral administration, in particular subcutaneous or intramuscular administration, in particular for the long term prevention or long term treatment of HIV infection.

Because of their pharmacokinetic properties and the need to keep plasma levels above a minimum level, currently used anti-HIV drugs require frequent administration of relatively high doses. The number and/or volume of dosage forms that need to be administered are commonly referred to as "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this also leads to the emergence of viral resistance. The problems associated with a high pill burden are prominent in anti-HIV therapy where a patient must take a large number of different anti-HIV agents.

Therefore, it would be desirable to provide HIV inhibitory therapy that reduces pill burden in that it involves the administration of dosage forms of relatively small size and additionally does not require frequent dosing. It would be attractive to provide anti-HIV therapy involving the administration of dosage forms at long time intervals such as one week or longer, or even one month or longer.

Currently, HIV cannot completely be eradicated so that persons infected with HIV pose a continuous risk of infecting others. After initial infection it takes a long time before the outbreak of the first symptoms of AIDS. People may live for years with the infection without experiencing any effects of it thereby being unaware of the risk of further transferring the virus to others. Prevention of HIV transmission therefore is crucial. Prevention currently focuses on avoiding transmission by sexual contacts, in particular by the use of condoms in populations at risk of being infected, on careful monitoring of blood samples for the presence of HIV and on avoiding of contact with blood of potentially infected subjects.

Despite these measures there is always an imminent risk of individuals being in contact with HIV infected persons of becoming infected. This in particular is the case for those providing medical care to infected patients or patients at risk of being infected such as physicians, nurses or dentists.

Hence there is a need for further means that provide prevention against transmission of HIV. There is a particular need for effective prevention means that are easy to apply. Providing such prevention means is another object of the present invention.

One embodiment of the present invention is therefore a freeze-dried nanosuspension as described in any of the above embodiments of the anti HIV drug 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof.

One embodiment of the present invention is a freeze-dried nanosuspension as described, whenever possible, in any of the above embodiments, of the anti HIV drug 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof, said freeze-dried nanosuspension further comprising a steric stabilizer, in particular poloxamer 338, and further optionally comprising a cryoprotectant, in particular polyvinylpyrrolidone, more in particular PVP K15 or PVP K17. For the concentrations of the anti HIV drug, the steric stabilizer and the cryoprotectant in the nanosuspension to be freeze-dried in order to obtain this freeze-dried nanosuspension, reference is made to the relevant sections hereinabove.

Said freeze-dried nanosuspension can be reconstituted to an aqueous nanosuspension by dilution with an aqueous dispersions medium, in particular water or water for injection. Said reconstituted nanosuspension can be used as a depot formulation, in particular as an injectable depot formulation, which may find use in the treatment of HIV infection as well as in the prevention against transmission of HIV.

These reconstituted nanosuspensions can intermittently be administered at time intervals of one week or longer that result in plasma levels that may be sufficient to suppress the growth (replication) of HIV. This allows for a reduced number of administrations thereby being beneficial in terms of pill burden and drug compliance of the patient. The nanoparticle formulations of 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof, of the invention therefore may be useful in the long-term treatment of HIV infection.

The intermittent administration of the reconstituted nanosuspension of 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof; at time intervals of one week or longer furthermore results in plasma levels that may be sufficient to provide prevention against transmission of HIV. Also in this instance, a reduced number of administrations is required, which again is advantageous in terms of pill burden and drug compliance of the individual at risk of being infected. The nanoparticle formulations of 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof, of the invention therefore may be useful in the long-term prevention of HIV infection.

In one embodiment, the present invention is concerned with a pharmaceutical composition for administration by intramuscular or subcutaneous injection, comprising a therapeutically effective amount of 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof, in the form of a reconstituted nanosuspension of 4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof; in a pharmaceutically acceptable aqueous carrier; wherein the nanosuspension is reconstituted from a freeze-dried nanosuspension comprising:

(a) 4-[[4-[[4-(2-cyanoethenyl)-2,6-dimethylphenyl]amino]-2-pyrimidinyl]-amino]benzonitrile or a stereoisomeric form thereof; or a pharmaceutically acceptable salt thereof; and
(b) a steric stabilizer which is a solid at room temperature; and
(c) optionally a cryoprotectant or lyoprotectant.

In one embodiment, the steric stabilizer in the above reconstituted nanosuspesnion is a crystalline solid at room temperature, in particular the steric stabilizer is a crystalline solid at room temperature and has a melting point equal to or above 30° C. or a melting point equal to or above 50° C. or a melting point equal to or above 75° C. or a melting point equal to or above 90° C.

In one embodiment, the steric stabilizer in the above reconstituted nanosuspension is an amorphous solid at room temperature, in particular the steric stabilizer is an amorphous solid at room temperature and has a glass transition temperature (Tg) equal to or above 30° C. or a Tg equal to or above 50° C. or a Tg equal to are above 75° C. or a Tg equal to or above 90° C.

In one embodiment, the steric stabilizer in the above reconstituted nanosuspesnion is poloxamer 338.

In one embodiment the above reconstituted nanosuspension further comprises a cryoprotectant or lyoprotectant, such as for example polyvinyl pyrrolidone, e.g. PVP K12, PVP K15 or PVP K17 or a mixture of PVP and a saccharide, such as for example trehalose.

The invention further concerns a method of treating a subject infected with HIV, said method comprising the administration, in particular by intramuscular or subcutaneous injection, of a pharmaceutical composition as specified above or hereinafter. Or, alternatively, the invention concerns the use of a pharmaceutical composition as specified above or hereinafter, for the manufacture of a medicament for treating HIV infection. Or, alternatively, the invention concerns a pharmaceutical composition as specified above or hereinafter for use in the treatment of HIV infection.

In another aspect, there is provided a method for the long term treatment of HIV infection, said method comprising the administration to a subject infected with HIV of an effective amount of a pharmaceutical composition as specified above or hereinafter, by intramuscular or subcutaneous injection; wherein the composition is administered or is to be administered intermittently at a time interval that is in the range of one week to one year, or one week to two years. Or, alternatively, the invention concerns the use of a pharmaceutical composition as specified above or hereinafter, for the manufacture of a medicament for the long term treatment of HIV infection and for administration by intramuscular or subcutaneous injection, wherein the medicament is administered or is to be administered intermittently at a time interval that is in the range of one week to one year, or one week to two years. Or alternatively, the invention concerns a pharmaceutical composition as specified above or hereinafter for use in the long term treatment of HIV infection, wherein the composition is for administration by intramuscular or subcutaneous injection, and wherein the composition is administered or is to be administered intermittently at a time interval that is in the range of one week to one year, or one week to two years.

The invention further concerns a method for the prevention of HIV infection in a subject at risk of being infected by HIV, said method comprising administering an effective amount, effective in preventing HIV infection, of a pharmaceutical composition as specified above or hereinafter, to said subject. Or alternatively, the invention concerns the use of a pharmaceutical composition as specified above or hereinafter for the manufacture of a medicament for the prevention of HIV infection in a subject at risk of being infected by HIV. Or, alternatively, the invention concerns a pharmaceutical composition as specified above or hereinafter for use in the prevention of HIV infection in a subject at risk of being infected by HIV.

In another aspect the invention relates to a method for the long term prevention of HIV infection in a subject at risk of being infected by HIV, said method comprising administering to said subject an effective amount, effective in preventing HIV infection, of a pharmaceutical composition as specified above or hereinafter, by intramuscular or subcutaneous injection; wherein the composition is administered or is to be administered intermittently at a time interval that is in the range of one week to one year, or one week to two years. Or alternatively, the present invention relates to the use of a pharmaceutical composition as specified above or hereinafter, for the manufacture of a medicament for the long term prevention of HIV infection in a subject at risk of being infected by HIV, and for administration by intramuscular or subcutaneous injection, wherein the medicament is administered or is to be administered intermittently at a time interval that is in the range of one week to one year or one week to two years. Or alternatively, the invention relates to a pharmaceutical composition as specified above or hereinafter for use in the long term prevention of HIV infection in a subject at risk of being infected by HIV, wherein the composition is for administration by intramuscular or subcutaneous injection, and wherein the composition is administered or is to be administered intermittently at a time interval that is in the range of one week to one year, or one week to two years.

In one embodiment the invention concerns a use or a method or a pharmaceutical composition for use as specified herein, wherein the pharmaceutical composition is administered or is to be administered at a time interval that is in the range of one week to one month, or in the range of one month to three months, or in the range of three months to six months, or in the range of six months to twelve months, or in the range of 12 months to 24 months.

In another embodiment the invention concerns a use or a method or a pharmaceutical composition for use as specified herein, wherein the pharmaceutical composition is administered or is to be administered once every two weeks, or once every month, or once every three months.

4-[[4-[[4-(2-cyanoethenyl)-2,6-dimethylphenyl]amino]-2-pyrimidinyl]-amino]benzonitrile can be used in base form or as a suitable pharmaceutically acceptable addition salt form, such as an acid addition salt form. The pharmaceutically acceptable addition salts are meant to comprise the therapeutically active non-toxic salt forms. The acid addition salt forms can be obtained by treating the base form with appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. A preferred form for use in the present invention is 4-[[4-[[4-(2-cyanoethenyl)-2,6-dimethylphenyl]amino]-2-pyrimidinyl]-amino]benzonitrile active ingredient in its base form.

4-[[4-[[4-(2-cyanoethenyl)-2,6-dimethylphenyl]amino]-2-pyrimidinyl]-amino]benzonitrile occurs in stereoisomeric forms, more in particular as E- and Z-isomeric forms. Both isomers may be used in the present invention. Whenever reference is made herein to 4-[[4-[[4-(2-cyanoethenyl)-2,6-dimethylphenyl]amino]-2-pyrimidinyl]amino]benzonitrile, the E- or the Z-form as well as any mixture of both forms are meant to be included. A preferred form of 4-[[4-[[4-(2-cyanoethenyl)-2,6-dimethylphenyl]amino]-2-pyrimidinyl] amino]benzonitrile for use in the present invention is the E-isomer, i.e. (E)-4-[[4-[[4-(2-cyanoethenyl)-2,6-dimethylphenyl]-amino]-2-pyrimidinyl]-amino]-benzonitrile, especially the E-isomer in base form, which may be referred to as rilpivirine. The Z-isomer of 4-[[4-[[4-(2-cyanoethenyl)-2,6-dimethylphenyl]amino]-2-pyrimidinyl]amino]benzonitrile, i.e. (Z)-4-[[4-[[4-(2-cyanoethenyl)-2,6-dimethylphenyl]-amino]-2-pyrimidinyl]-amino]-benzonitrile, can also be used.

Whenever reference is made herein to the E-form of 4-[[4-[[4-(2-cyanoethenyl)-2,6-dimethylphenyl]amino]-2-pyrimidinyl]amino]benzonitrile, the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of 4-[[4-[[4-(2-cyanoethenyl)-2,6-dimethylphenyl]amino]-2-pyrimidinyl]amino]benzonitrile, the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. The Z-form substantially free of the E-form can also be used. Substantially free in this context refers to E-Z-mixtures with no or almost no E-form, e.g. isomeric mixtures containing as much as 90%, in particular 95% or even 98% or 99% of the Z-form. In one embodiment, 4-[[4-[[4-(2-cyanoethenyl)-2,6-dimethylphenyl]amino]-2-pyrimidinyl]amino]benzonitrile active ingredient is used in the E-form, in particular the E-form of 4-[[4-[[4-(2-cyanoethenyl)-2,6-dimethylphenyl]amino]-2-pyrimidinyl]amino] benzonitrile base.

Also meant to be included for use in this invention are salts of the stereoisomeric forms of 4-[[4-[[4-(2-cyanoethenyl)-2,6-dimethylphenyl]amino]-2-pyrimidinyl]-amino] benzonitrile, in particular the salts mentioned above of the Z or E isomeric form of 4-[[4-[[4-(2-cyanoethenyl)-2,6-dimethylphenyl]amino]-2-pyrimidinyl]-amino]benzonitrile, such as for example the hydrochloric acid salt of E-4-[[4-[[4-(2-cyanoethenyl)-2,6-dimethylphenyl]amino]-2-pyrimidinyl]amino]benzonitrile.

Whenever used herein below, 4-[[4-[[4-(2-cyanoethenyl)-2,6-dimethylphenyl]amino]-2-pyrimidinyl]amino]benzonitrile also comprises a stereoisomeric form thereof; or a pharmaceutically acceptable salt thereof, unless otherwise indicated.

It has been found that the physico-chemical properties of 4-[[4-[[4-(2-cyanoethenyl)-2,6-dimethylphenyl]amino]-2-pyrimidinyl]amino]benzonitrile allow for the manufacture of nanosuspensions that have unique pharmacokinetic properties in that they can be used for the long-term treatment of HIV infection as well as for the long-term prevention of HIV infection and to this purpose only a limited number of drug administrations is required. This is beneficial in terms of pill-burden as well as patient compliance with the prescribed dose regimen.

As used herein the term "treatment of HIV infection" relates to the treatment of a subject being infected with HIV. The term "treatment of HIV infection" also relates to the treatment of diseases associated with HIV infection, for example AIDS, or other conditions associated with HIV infection including thrombocytopaenia, Kaposi's sarcoma and infection of the central nervous system characterized by progressive demyelination, resulting in dementia and symptoms such as, progressive dysarthria, ataxia and disorientation, and further conditions where HIV infection has also been associated with, such as peripheral neuropathy, progressive generalized lymphadenopathy (PGL), and AIDS-related complex (ARC).

The term "prevention of HIV infection" relates to the prevention or avoidance of a subject becoming infected with HIV. The source of infection can be various, a material containing HIV, in particular a body fluid that contains HIV such as blood or sperm, or another subject who is infected with HIV. Prevention of HIV infection relates to the prevention of the transmission of the virus from the material containing HIV or from the HIV infected individual to an uninfected person, or relates to the prevention of the virus from entering the body of an uninfected person. Transmission of the HIV virus can be by any known cause of HIV transfer such as by sexual transmission or by contact with blood of an infected subject, e.g. medical staff providing care to infected subjects. Transfer of HIV can also occur by contact with HIV infected blood, e.g. when handling blood samples or with blood transfusion. It can also be by contact with infected cells, e.g. when carrying out laboratory experiments with HIV infected cells.

The terms "treatment of HIV infection", "anti-HIV therapy", as well as similar terms, refer to a treatment by which the viral load of HIV (represented as the number of copies of viral RNA in a specified volume of serum) is reduced. The more effective the treatment, the lower the viral load. Preferably the viral load should be reduced to as low levels as possible, e.g. below about 200 copies/ml, in particular below about 100 copies/ml, more in particular below 50 copies/ml, if possible below the detection limit of the virus. Reductions of viral load of one, two or even three orders of magnitude (e.g. a reduction in the order of about 10 to about $10^2$, or more, such as about $10^3$) are an indication of the effectiveness of the treatment. Another parameter to measure effectiveness of anti-HIV treatment is the CD4 count, which in normal adults ranges from 500 to 1500 cells per μl. Lowered CD4 counts are an indication of HIV infection and once below about 200 cells per μl, AIDS may develop. An increase of CD4 count, e.g. with about 50, 100, 200 or more cells per μl, is also an indication of the effectiveness of anti-HIV treatment. The CD4 count in particular should be increased to a level above about 200 cells per μl, or above about 350 cells per μl. Viral load or CD4 count, or both, can be used to diagnose the degree of HIV infection.

The terms "effective treatment of HIV" and similar terms refer to that treatment that lowers the viral load, or increases CD4 count, or both, as described above. The terms "effective prevention of HIV" and similar terms refer to that situation where there is a decrease in the relative number of newly infected subjects in a population in contact with a source of HIV infection such as a material containing HIV, or a HIV infected subject. Effective prevention can be measured, for example, by measuring in a mixed population of HIV infected and non-infected individuals, if there is a decrease of the relative number of newly infected individuals, when comparing non-infected individuals treated with a pharmaceutical composition of the invention, and non-treated non-infected individuals. This decrease can be measured by statistical analysis of the numbers of infected and non-infected individuals in a given population over time.

The terms "therapeutically effective amount", "an effective amount", "an amount, effective in preventing HIV infection", and similar terms, refer to amounts of the active ingredient 4-[[4-[[4-(2-cyanoethenyl)-2,6-dimethylphenyl]amino]-2-pyrimidinyl]-amino]benzonitrile that result in efficacious blood plasma levels. With "efficacious blood plasma levels" is meant those blood plasma levels of the HIV inhibitor 4-[[4-[[4-(2-cyanoethenyl)-2,6-dimethylphenyl]amino]-2-pyrimidinyl]amino]benzonitrile that provide effective treatment or effective prevention of HIV infection.

The term "subject" in particular relates to a human being.

The average particle size of the nanoparticles of the nanosuspensions to be freeze dried or the nanosuspension resulting from reconstitution of the freeze-dried nanosuspension may be below about 1000 nm, or below about 500 nm, or below about 400 nm, or below about 300 nm, or below about 200 nm. Preferably, the average particle size is about 200 nm or about 400 nm or about 800 nm, more preferably about 200 nm.

As used herein, the term average particle size has its conventional meaning as known to the person skilled in the art and can be measured by art-known particle size measuring techniques such as, for example, sedimentation field flow fractionation, photon correlation spectroscopy, laser diffraction or disk centrifugation. The average particle sizes mentioned herein may be related to volume distributions of the particles. In that instance, by "an average particle size of less than about 50 µm" it is meant that at least 50% of the volume of the particles has a particle size of less than about 50 µm, and the same applies to the other particle sizes mentioned. In a similar manner, the average particle sizes may be related to weight distributions of the particles. In that instance, by "an average particle size of less than about 50 µm" it is meant that at least 50% of the weight of the particles has a particle size of less than about 50 µm, and the same applies to the other particle sizes mentioned. Usually volume and weight distribution result in the same or about the same value for the average particle size.

The pharmaceutical compositions of the present invention provide release of the active ingredient 4-[[4-[[4-(2-cyanoethenyl)-2,6-dimethylphenyl]amino]-2-pyrimidinyl]-amino]benzonitrile over a prolonged period of time and therefore they can also be referred to as sustained or delayed release compositions. After administration, the compositions of the invention stay in the body and steadily release 4-[[4-[[4-(2-cyanoethenyl)-2,6-dimethylphenyl]amino]-2-pyrimidinyl]amino]benzonitrile, keeping such levels of this active ingredient in the patient's system for a prolonged period of time, thereby providing, during said period, anti-HIV therapy or prevention of HIV infection. Because of the fact that the pharmaceutical compositions of the invention stay in the body and steadily release 4-[[4-[[4-(2-cyanoethenyl)-2,6-dimethylphenyl]amino]-2-pyrimidinyl]amino]benzonitrile, they can be referred to as pharmaceutical compositions suitable as depot formulations.

As used herein with the term "prolonged period of time", there is meant a term (or time period) that may be in the range of one week up to one year or up to two years, or a term in the range of one to two weeks, or two to three weeks, or three to four weeks, or a term in the range of one to two months, or two to three months, or three to four months, or three to six months, or six months to 12 months, or 12 months to 24 months, or a term that is in the range of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months.

The pharmaceutical compositions of this invention may be applied in the long-term treatment or the long-term prevention of HIV infection, or with other words they may be used in the treatment of HIV infection, or in the prevention of HIV infection, during a prolonged period of time. The compositions of the invention are effective in anti-HIV therapy or in the prevention of HIV infection for a prolonged period of time, for example for at least about one week or longer, or for about 1 month or longer. By the expression "effective for at least about one week or longer", one means that the plasma level of the active ingredient, 4-[[4-[[4-(2-cyanoethenyl)-2,6-dimethylphenyl]amino]-2-pyrimidinyl]amino]benzonitrile, should be above a threshold value. In case of therapeutic application said threshold value is the lowest plasma level at which 4-[[4-[[4-(2-cyanoethenyl)-2,6-dimethylphenyl]amino]-2-pyrimidinyl]amino]benzonitrile provides effective treatment of HIV infection. In case of application in the prevention of HIV infection said threshold value is the lowest plasma level at which 4-[[4-[[4-(2-cyanoethenyl)-2,6-dimethylphenyl]amino]-2-pyrimidinyl]amino]benzonitrile is effective in preventing transmission of HIV infection.

With "long term" for example as used in relation to "long term prevention of HIV infection" or "long term treatment of HIV infection", or similar terminology, there are meant terms that may be in the range of one week up to one year or up to two years, or longer, such as five or 10 years. In particular in the case of treatment of HIV infection, such terms will be long, in the order of one to several years. Such terms may also be relatively short, in particular in the case of prevention. Shorter terms are those of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months. In one embodiment the methods and uses in accordance with the present invention are for the prevention of HIV infection during one month, or several months, e.g. 2, 3, 4, 5 or six months or even longer, e.g. 7, 8, 9 or 12 months. In one embodiment the methods and uses in accordance with the present invention are for the treatment of HIV infection during one month, or several months, e.g. 2, 3, 4, 5 or six months or even longer, e.g. 7, 8, 9 or 12 months.

The pharmaceutical compositions of the present invention can be administered at various time intervals. When used in the prevention of HIV infection, the pharmaceutical compositions of this invention can be administered only once or a limited number of times such as twice, three, four, five or six times, or more. This may be recommendable where prevention is required during a limited period of time, such as the period during which there is a risk of infection.

The pharmaceutical compositions of the present invention can be administered at the time intervals mentioned above, such as at a time interval that is in the range of one week to one month, or in the range of one month to three months, or in the range of three months to six months, or in the range of six months to twelve months. In one embodiment, the pharmaceutical composition can be administered once every two weeks, or once every month, or once every three months. In another embodiment the time interval is in the range of one to two weeks, or two to three weeks, or three to four weeks, or the time interval is in the range of one to two months, or two to three months, or three to four months, or three to six months, or six months to 12 months, or 12 months to 24 months. The time interval may be at least one week, but may also be several weeks, e.g. 2, 3, 4, 5 or 6 weeks, or at time intervals of one month, or of several months, e.g. 2, 3, 4, 5 or 6 months or even longer, e.g. 7, 8, 9 or 12 months. In one embodiment, the pharmaceutical compositions of the present invention are administered at a time interval of one, two or three months. These longer periods between each administration of the pharmaceutical compositions of the invention provide further improvements in terms of pill burden and compliance. To further improve compliance, patients can be instructed to take their medication at a certain day of the week, where the composition is administered on a weekly schedule, or at a certain day of the month in case of a monthly schedule.

The length of the time intervals between each administration of a composition of the present invention may vary. For example said time intervals may be selected in function of the blood plasma levels. The intervals may be shorter where the blood plasma levels of 4-[[4-[[4-(2-cyanoethenyl)-2,6-dimethylphenyl]amino]-2-pyrimidinyl]amino]benzonitrile are deemed too low, e.g. when these approach the minimum blood plasma level specified hereinafter. The intervals may be longer where the blood plasma levels of 4-[[4-[[4-(2-cyanoethenyl)-2,6-dimethylphenyl]amino]-2-pyrimidinyl]amino]benzonitrile are deemed too high. In one embodiment, the compositions of the invention are administered at equal time intervals. The compositions may be administered without any interjacent additional administrations, or with other words, the compositions may be administered at particular points in time separated from one another by a time period of varying or equal length, e.g. a time period of at least one week, or any other time period specified herein, during which no further 4-[[4-[[4-(2-cyanoethenyl)-2,6-dimethylphenyl]amino]-2-pyrimidinyl]-amino]benzonitrile is administered. Having time intervals of the same length has the advantage that the administration schedule is simple, e.g. administration takes place at the same day in the week, or the same day in the month. Such administration schedule therefore involves limited "pill burden" thereby contributing beneficially to the patient's compliance to the prescribed dosing regimen.

The concentration (or "C") of 4-[[4-[[4-(2-cyanoethenyl)-2,6-dimethylphenyl]amino]-2-pyrimidinyl]amino]benzonitrile in the blood plasma of a subject treated therewith is generally expressed as mass per unit volume, typically nanograms per milliliter (ng/ml). For convenience, this concentration may be referred to herein as "blood plasma drug concentration" or "blood plasma concentration".

The dose (or amount) of 4-[[4-[[4-(2-cyanoethenyl)-2,6-dimethylphenyl]amino]-2-pyrimidinyl]amino]benzonitrile administered, depends on the amount of the drug in the pharmaceutical compositions of the invention, or on the amount of a given composition that is administered. Where higher blood plasma levels are desired, either or both of a composition of higher 4-[[4-[[4-(2-cyanoethenyl)-2,6-dimethylphenyl]amino]-2-pyrimidinyl]amino]benzonitrile concentration, or more of a given composition, may be administered. This applies vice versa if lower plasma levels are desired. Also a combination of varying time intervals and varying dosing may be selected to attain certain desired blood plasma levels.

The dose (or amount) of 4-[[4-[[4-(2-cyanoethenyl)-2,6-dimethylphenyl]amino]-2-pyrimidinyl]amino]benzonitrile administered also depends on the frequency of the administrations (i.e. the time interval between each administration). Usually, the dose will be higher where administrations are less frequent. All these parameters can be used to direct the blood plasma levels to desired values The dosing regimen also depends on whether prevention or treatment of HIV infection is envisaged. In case of therapy, the dose of 4-[[4-[[4-(2-cyanoethenyl)-2,6-dimethylphenyl]amino]-2-pyrimidinyl]amino]benzonitrile administered or the frequency of dosing, or both, are selected so that the blood plasma concentration of 4-[[4-[[4-(2-cyanoethenyl)-2,6-dimethylphenyl]amino]-2-pyrimidinyl]amino]benzonitrile is kept above a minimum blood plasma level. The term "minimum blood plasma level" (or $C_{min}$) in this context refers to the blood plasma level of 4-[[4-[[4-(2-cyanoethenyl)-2,6-dimethylphenyl]amino]-2-pyrimidinyl]amino]benzonitrile that provides effective treatment of HIV. In particular, the blood plasma level of 4-[[4-[[4-(2-cyanoethenyl)-2,6-dimethylphenyl]amino]-2-pyrimidinyl]amino]benzonitrile is kept at a level above a minimum blood plasma level of about 10 ng/ml, or above about 15 ng/ml, or above about 20 ng/ml, or above about 40 ng/ml, or above about 50 ng/ml, or above about 90 ng/ml, or above about 270 ng/ml, or above about 540 ng/ml In one embodiment, the blood plasma level of 4-[[4-[[4-(2-cyanoethenyl)-2,6-dimethylphenyl]amino]-2-pyrimidinyl]amino]benzonitrile is kept above a level of about 90 ng/ml. Or the blood plasma level of 4-[[4-[[4-(2-cyanoethenyl)-2,6-dimethylphenyl]amino]-2-pyrimidinyl]-amino]benzonitrile may be kept within certain ranges, in particular ranges starting from a minimum blood plasma level selected from those mentioned above and ending at a higher blood plasma levels selected from those mentioned above and selected from 500 ng/ml and 1000 ng/ml (e.g. from 10 to 15, 10 to 20, 10 to 40, etc., or from 15 to 20, or 15 to 40, or 15 to 90, etc., or 20 to 40, 20 to 90, or 20 to 270, etc., or 40 to 90, 40 to 270, or 40-540, etc., each time from about the indicated value in ng/ml to about the indicated value in ng/ml). In one embodiment said range is from about 10 to about 20, from about 20 to about 90, from about 90 to about 270, from about 270 to about 540, from about 540 to about 1000, each time from about the indicated value in ng/ml to about the indicated value in ng/ml.

The plasma levels of 4-[[4-[[4-(2-cyanoethenyl)-2,6-dimethylphenyl]amino]-2-pyrimidinyl]amino]benzonitrile should be kept above the above-mentioned minimum blood plasma levels because at lower levels the virus may no longer be sufficiently suppressed so that it can multiply with the additional risk of the emergence of mutations.

In the instance of HIV prevention, the term "minimum blood plasma level" (or $C_{min}$) refers to the lowest blood plasma level of 4-[[4-[[4-(2-cyanoethenyl)-2,6-dimethylphenyl]amino]-2-pyrimidinyl]amino]benzonitrile that provides effective prevention of HIV infection. In the case of transmission of HIV from a material containing HIV or from a subject infected by HIV to a subject not infected by HIV, this is the lowest blood plasma level that is effective in inhibiting said transmission.

In particular, in the instance of HIV prevention, the blood plasma level of 4-[[4-[[4-(2-cyanoethenyl)-2,6-dimethylphenyl]amino]-2-pyrimidinyl]amino]benzonitrile can be kept at a level above a minimum blood plasma level mentioned above in relation to therapy. However in prevention the blood plasma level of 4-[[4-[[4-(2-cyanoethenyl)-2,6-dimethylphenyl]amino]-2-pyrimidinyl]amino]benzonitrile can be kept at a lower level, for example at a level above about 4 ng/ml, or about 5 ng/ml, or about 8 ng/ml. The blood plasma levels of 4-[[4-[[4-(2-cyanoethenyl)-2,6-dimethylphenyl]amino]-2-pyrimidinyl]amino]benzonitrile should preferably be kept above these minimum blood plasma levels because at lower levels the drug may no longer be effective thereby increasing the risk of transmission of HIV infection. Plasma levels of TMC278 may be kept at somewhat higher levels to have a safety margin. Such higher levels start from about 50 ng/ml or more; or from about 90 ng/ml or more. The blood plasma level of 4-[[4-[[4-(2-cyanoethenyl)-2,6-dimethylphenyl]amino]-2-pyrimidinyl]amino]benzonitrile can be kept at a level that is in the ranges mentioned above in relation to therapy, but where the lower limits include the blood plasma levels of about 4 ng/ml, or about 5 ng/ml, or about 8 ng/ml.

An advantage of 4-[[4-[[4-(2-cyanoethenyl)-2,6-dimethylphenyl]amino]-2-pyrimidinyl]amino]benzonitrile is that it can be used up to relatively high blood plasma levels without any significant side effects. The plasma concentrations of 4-[[4-[[4-(2-cyanoethenyl)-2,6-dimethylphenyl]amino]-2-pyrimidinyl]amino]benzonitrile may reach relatively high levels, but as with any drug should not exceed a maximum plasma level (or $C_{max}$), which is the blood plasma level where 4-[[4-[[4-(2-cyanoethenyl)-2,6-dimethylphenyl]amino]-2-pyrimidinyl]amino]benzonitrile causes significant side effects. As used herein, the term "significant side effects" means that the side effects are present in a relevant patient population to an extend that the side effects affect the patients' normal functioning. The $C_{max}$ for 4-[[4-[[4-(2-cyanoethenyl)-2,6-dimethylphenyl]amino]-2-pyrimidinyl]amino]benzonitrile can be determined from the extrapolation of test data in cellular assays or from the evaluation of clinical testing and preferably should not exceed a value of about 500 ng/ml or 1000 ng/ml. In an embodiment, the amount and the frequency of administrations of 4-[[4-[[4-(2-cyanoethenyl)-2,6-dimethylphenyl]amino]-2-pyrimidinyl]amino]benzonitrile to be administered are selected such that the blood plasma concentrations are kept during a long term at a level comprised between a maximum plasma level (or $C_{max}$ as specified above) and a minimum blood plasma level (or $C_{min}$ as specified above).

In certain instances it may be desirable to keep the plasma levels of 4-[[4-[[4-(2-cyanoethenyl)-2,6-dimethylphenyl]amino]-2-pyrimidinyl]amino]benzonitrile at relatively low levels, e.g. as close as possible to the minimum blood plasma levels specified herein. This will allow reducing the frequency of the administrations and/or the quantity of 4-[[4-[[4-(2-cyanoethenyl)-2,6-dimethylphenyl]amino]-2-pyrimidinyl]-amino]benzonitrile administered with each administration. It will also allow avoiding undesirable side effects, which will contribute to the acceptance of the dosage forms in most of the targeted population groups who are healthy people at risk of being infected and therefore are less inclined to tolerate side effects. The plasma levels of 4-[[4-[[4-(2-cyanoethenyl)-2,6-dimethylphenyl]amino]-2-pyrimidinyl]amino]benzonitrile may be kept at relatively low levels in the instance of prevention. One embodiment concerns uses or methods for prevention of HIV infection, as specified above or hereinafter, wherein the minimum blood plasma level of 4-[[4-[[4-(2-cyanoethenyl)-2,6-dimethylphenyl]amino]-2-pyrimidinyl]amino]benzonitrile is as specified herein and the maximum blood plasma level is about equal to the lowest blood plasma level that causes the RT inhibitor to act therapeutically, also as specified herein.

In other embodiments, the blood plasma level of 4-[[4-[[4-(2-cyanoethenyl)-2,6-dimethylphenyl]amino]-2-pyrimidinyl]amino]benzonitrile is kept at a level below a lower maximum blood plasma level of about 10 ng/ml, more in particular about 15 ng/ml, further in particular about 20 ng/ml, still more in particular about 40 ng/ml. In a particular embodiment, the blood plasma level of 4-[[4-[[4-(2-cyanoethenyl)-2,6-dimethylphenyl]amino]-2-pyrimidinyl]amino]benzonitrile is kept below a level of about 13.5 ng/ml. In one embodiment, the plasma level of 4-[[4-[[4-(2-cyanoethenyl)-2,6-dimethylphenyl]amino]-2-pyrimidinyl]amino]benzonitrile is kept in an interval of the lower maximum blood level specified above, and the minimum blood plasma levels mentioned in relation to prevention. For example the blood plasma levels of 4-[[4-[[4-(2-cyanoethenyl)-2,6-dimethylphenyl]amino]-2-pyrimidinyl]amino] benzonitrile are kept below about 10 ng/ml and above a minimum level of about 4 ng/ml.

In other instances it may be desirable to keep the plasma levels of 4-[[4-[[4-(2-cyanoethenyl)-2,6-dimethylphenyl]amino]-2-pyrimidinyl]amino]benzonitrile at relatively higher levels, for example where there is a high risk of infection and more frequent and/or higher doses are not an issue. In these instances the minimum blood plasma level may be equal to the lowest blood plasma level of 4-[[4-[[4-(2-cyanoethenyl)-2,6-dimethylphenyl]amino]-2-pyrimidinyl]amino]benzonitrile that provides effective treatment of HIV, such as the specific levels mentioned herein.

In the instance of prevention, the dose of 4-[[4-[[4-(2-cyanoethenyl)-2,6-dimethylphenyl]amino]-2-pyrimidinyl]amino]benzonitrile, in particular rilpivirine, to be administered should be calculated on a basis of about 0.2 mg/day to about 50 mg/day, or 0.5 mg/day to about 50 mg/day, or of about 1 mg/day to about 10 mg/day, or of about 10 mg/day to about 20 mg/day, or of about 15 mg/day to about 25 mg/day, or of about 20 mg/day to about 25 mg/day, or of about 2 mg/day to about 5 mg/day, e.g. about 3 mg/day or about 5 mg/day or about 20 mg/day. This corresponds to a weekly dose of about 1.5 mg to about 350 mg, in particular of about 3.5 mg to about 350 mg, in particular of about 7 mg to about 70 mg, or of about 70 mg to about 140 mg, or of about 105 mg to about 175 mg, or of about 140 mf to about 175 mg, or of about 14 mg to about 35 mg, e.g. about 21 mg or about 35 mg or about 140 mg, or to a monthly dose of from 6 mg to about 3000 mg, in particular about 15 mg to about 1,500 mg, more in particular of about 30 mg to about 300 mg, or about 300 mg to about 600 mg, or of about 450 mg to about 750 mg, or of about 600 mg to about 750 mg, or of about 60 mg to about 150 mg, e.g. about 90 mg or about 150 mg or about 600 mg. Doses for other dosing regimens can readily be calculated by multiplying the daily dose with the number of days between each administration.

In the instance of therapy, the dose of 4-[[4-[[4-(2-cyanoethenyl)-2,6-dimethylphenyl]amino]-2-pyrimidinyl]amino]benzonitrile, in particular rilpivirine, to be administered should be somewhat higher and should be calculated on a basis of about 1 mg/day to about 150 mg/day, or of about 2 mg/day to about 100 mg/day, or of about 5 mg/day to about 50 mg/day, or about 10 mg/day to about 25 mg/day, or of about 15 mg/day to about 25 mg/day, or of about 20 mg/day to about 25 mg/day, e.g. about 15 mg/day or about 20 mg/day or about 25 mg/day. The corresponding weekly or monthly doses can be calculated as set forth above. For applications in prevention, the doses may be lower although the same dosing as for therapeutic applications may be used.

In one embodiment, the monthly dose of 4-[[4-[[4-(2-cyanoethenyl)-2,6-dimethylphenyl]amino]-2-pyrimidinyl]amino]benzonitrile, in particular rilpivirine, is 600 mg. In one embodiment, the concentration of 4-[[4-[[4-(2-cyanoethenyl)-2,6-dimethylphenyl]amino]-2-pyrimidinyl]amino]benzonitrile, in particular rilpivirine, in the aqueous reconstituted nanosuspension is 200 mg/ml or 300 mg/ml.

It has been found that, once administered, the blood plasma levels of 4-[[4-[[4-(2-cyanoethenyl)-2,6-dimethylphenyl]amino]-2-pyrimidinyl]amino]benzonitrile are more or less stable, i.e. they fluctuate within limited margins. The blood plasma levels have been found to approach more or less a steady state mode or to approximate more or less a zero order release rate during a prolonged period of time. By "steady state" is meant the condition in which the amount of drug present in the blood plasma of a subject stays at more or less the same level over a prolonged period of time. The plasma levels of 4-[[4-[[4-(2-cyanoethenyl)-2,6-dimethylphenyl]amino]-2-pyrimidinyl]-amino]benzonitrile generally do not show any drops below the minimum plasma level at which the drug is effective. The term "stays at more or less the same level" does not exclude that there can be small fluctuations of the plasma concentrations within an acceptable range, e.g. fluctuations within a range of about +/−30%, or about +/−20%, or about +/−10%, or about +/−10%.

In some instances there may be an initial plasma concentration peak after administration, after which the plasma levels achieve a "steady-state", as mentioned hereinbefore.

The compositions of the invention show good local tolerance and ease of administration. Good local tolerance relates to minimal irritation and inflammation at the site of injection; ease of administration refers to the size of needle and length of time required to administer a dose of a particular drug formulation.

In one embodiment, the nanoparticles in the compositions of the invention mainly comprise crystalline 4-[[4-[[4-(2-cyanoethenyl)-2,6-dimethylphenyl]amino]-2-pyrimidinyl]amino]benzonitrile; and a steric stabilizer, the combined amount of which may at least comprise by weight about 50%, or at least about 80%, or at least about 90%, or at least about 92%, or at least about 95%, or at least about 98%, or at least about 99%, or at least about 99.5% of the nano particles.

The reconstituted pharmaceutical compositions according to the present invention contain a carrier, in particular an aqueous carrier that preferably is pharmaceutically acceptable. Said aqueous carrier comprises sterile water optionally in admixture with other pharmaceutically acceptable ingredients. The latter comprise any ingredients for use in injectable formulations or I suspension formulations or in oral formulations. These ingredients may be selected from one or more of a suspending agent, a buffer, a pH adjusting agent, a preservative, an isotonizing agent, and the like ingredients. In one embodiment, said ingredients are selected from one or more of a suspending agent, a buffer, a pH adjusting agent, and optionally, a preservative and an isotonizing agent. Particular ingredients may function as two or more of these agents simultaneously, e.g. behave like a preservative and a buffer, or behave like a buffer and an isotonizing agent. As stated above, the other pharmaceutically acceptable ingredients may also be present in the freeze-dried drug nanosuspension itself. Or the other pharmaceutically acceptable ingredients may be present in both the freeze-dried drug nanosuspension itself as well as in the carrier, in particular the aqueous carrier. Preferably, the other pharmaceutically acceptable ingredients are present in the freeze-dried drug nanosuspension as such.

Suitable buffering agents and pH adjusting agents should be used in amount sufficient to render the dispersion neutral to very slightly basic (up to pH 8.5), preferably in the pH range of 7 to 7.5. Particular buffers are the salts of week acids. Buffering and pH adjusting agents that can be added may be selected from tartaric acid, maleic acid, glycine, sodium lactate/lactic acid, ascorbic acid, citric acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl)aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, including mixtures thereof.

Preservatives comprise antimicrobials and anti-oxidants which can be selected from the group consisting of benzoic acid, benzyl alcohol, butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-piccolinium chloride, phenylmercuric acetate and thimerosal. Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfate, isoacorbic acid, hydroxypropyl cyclodextrin. Chelating agents include sodium citrate, sodium EDTA and malic acid. Citric acid can be used as anti-oxidant, buffer and isotonizing agent.

An isotonizing agent or isotonifier may be present to ensure isotonicity of the pharmaceutical compositions of the present invention, and includes sugars such as glucose, dextrose, sucrose, fructose, trehalose, lactose; polyhydric sugar alcohols, preferably trihydric or higher sugar alcohols, such as glycerin, erythritol, arabitol, xylitol, sorbitol and mannitol. Alternatively, sodium chloride, sodium sulfate, or other appropriate inorganic salts may be used to render the solutions isotonic. These isotonifiers can be used alone or in combination. The suspensions conveniently comprise from 0 to 10% (w/v), in particular 0 to 6% of isotonizing agent. Of interest are nonionic isotonifiers, e.g. glucose or trehalose, as electrolytes may affect colloidal stability.

A desirable feature for a pharmaceutical composition of the invention relates to the ease of administration. The viscosity of the pharmaceutical compositions of the invention should preferably be sufficiently low to allow administration by injection. In particular they should be designed so that they can be taken up easily in a syringe (e.g. from a vial), injected through a fine needle (e.g. a 20 G 1½, 21 G 1½, 22 G 2 or 22 G 1¼ needle) in not too long a time span. In one embodiment the viscosity of the compositions of the invention is below about 75 mPa·s, or below 60 mPa·s. Aqueous suspensions of such viscosity or lower usually meet the above-mentioned criteria.

Ideally, the reconstituted aqueous suspensions according to the present invention will comprise as much 4-[[4-[[4-(2-cyanoethenyl)-2,6-dimethylphenyl]amino]-2-pyrimidinyl]amino]benzonitrile as can be tolerated so as to keep the injected volume to a minimum, in particular from 3 to 50% (w/v), or from 3 to 40% (w/v), or from 3 to 30% (w/v), or from 3 to 20% (w/v), or from 10 to 40% (w/v), or from 10 to 30% (w/v), of 4-[[4-[[4-(2-cyanoethenyl)-2,6-dimethylphenyl]amino]-2-pyrimidinyl]-amino]benzonitrile. In one embodiment the reconstituted aqueous suspensions of the invention contain about 10% (w/v) of 4-[[4-[[4-(2-cyanoethenyl)-2,6-dimethylphenyl]amino]-2-pyrimidinyl]amino]benzonitrile, or about 20% (w/v) of 4-4-[[4-[[4-(2-cyanoethenyl)-2,6-dimethylphenyl]amino]-2-pyrimidinyl]-amino]benzonitrile, or about 30% (w/v) of 4-[[4-[[4-(2-cyanoethenyl)-2,6-dimethylphenyl]amino]-2-pyrimidinyl]amino]benzonitrile.

In one embodiment, the reconstituted aqueous nanosuspensions may comprise by weight, based on the total volume of the composition:
(a) from 3% to 50% (w/v), or from 10% to 40% (w/v), or from 10% to 30% (w/v), or 10% (w/v), or 20% (w/v), or 30% (w/v) of 4-[[4-[[4-(2-cyanoethenyl)-2,6-dimethylphenyl]amino]-2-pyrimidinyl]amino]benzonitrile, in particular of rilpivirine;
(b) from 0.5% to 10%, or from 0.5% to 2% (w/v), or 3% (w/v), or 5% (w/v) of a steric stabilizer according to the present invention, e.g. a poloxamer, e.g. poloxamer 338;
(c) from 0 to 20% (w/v), or from 0 to 10% (w/v), or 5% (w/v) of a cryoprotectant or lyoprotectant, e.g. PVP;
(d) from 0% to 10%, or from 0% to 5%, or from 0% to 2%, or from 0% to 1% of one or more buffering agents;
(e) from 0% to 10%, or from 0% to 6% (w/v) of an isotonizing agent;
(f) from 0% to 2% (w/v) of a preservative; and
(g) water for injection q.s. ad 100% (w/v).

To the suspensions may optionally be added an amount of acid or base to bring the pH to a value of about pH 7. Suitable acids or bases are any of those that are physiologically acceptable, e.g. HCl, HBr, sulfuric acid, alkali metal hydroxides such as NaOH.

The administration of 4-[[4-[[4-(2-cyanoethenyl)-2,6-dimethylphenyl]amino]-2-pyrimidinyl]amino]benzonitrile as in the present invention may suffice to treat HIV infection although in a number of cases it may be recommendable to co-administer other HIV inhibitors. The latter preferably include HIV inhibitors of other classes, in particular those selected from NRTIs, PIs and fusion inhibitors. In one embodiment, the other HIV inhibitor that is co-administered is a PI inhibitor. HIV inhibitors that may be co-administered by preference are those used in HAART combinations comprising an NNRTI. For example two further NRTIs or an NRTI and a PI may be co-administered. Such co-administration may be by oral administration or parenterally, including parenteral administration for long term treatment of HIV infection or long term prevention of HIV infection.

In certain instances, the treatment of HIV infection may be limited to only the administration of a composition of 4-[[4-[[4-(2-cyanoethenyl)-2,6-dimethylphenyl]amino]-2-pyrimidinyl]amino]benzonitrile in accordance with this invention, i.e. as monotherapy without co-administration of further HIV inhibitors. This option may be recommended, for example, where the viral load is relatively low, for example where the viral load (represented as the number of copies of viral RNA in a specified volume of serum) is below about 200 copies/ml, in particular below about 100 copies/ml, more in particular below 50 copies/ml, specifically below the detection limit of the virus. In one embodiment, this type of monotherapy is applied after initial treatment with a combination of HIV drugs, in particular with any of the HAART combinations during a certain period of time until the viral load in blood plasma reaches the afore mentioned low viral level.

In a further aspect the present invention relates to the use of a reconstituted pharmaceutical composition comprising an anti-virally effective amount of 4-[[4-[[4-(2-cyanoethenyl)-2,6-dimethylphenyl]amino]-2-pyrimidinyl]amino]benzonitrile, in accordance with the present invention, for the manufacture of a medicament for maintenance therapy of a subject being infected with HIV, wherein the composition is administered or is to be administered intermittently at a time interval that is in the range of one week to one year, or one week to two years.

Thus in a further aspect, the present invention provides a method for the long term treatment of a patient being infected with HIV, said method comprising
(i) the treatment of said patient with a combination of HIV inhibitors; followed by
(ii) the intermittent administration of a pharmaceutical composition comprising an anti-virally effective amount of 4-[[4-[[4-(2-cyanoethenyl)-2,6-dimethylphenyl]amino]-2-pyrimidinyl]amino]benzonitrile in accordance with the present invention, wherein the composition is administered at a time interval of at least one week, or at least 2 weeks or once every month or once every 3 months.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

Experimental Part 1

The following examples are intended to illustrate the present invention and should not be construed as limiting the invention thereto.

Materials and Methods

Two poorly water-soluble crystalline API's:Itraconazole and Rilpivirine. 0.3 mm yttrium stabilized zirconia beads. Lutrol F108 Prill (Poloxamer 338) and Cremophor EL (BASF, Ludwigshafen, Germany). PVP K15, trehalose and sucrose of analytical grade (Sigma Chemical Company, Munich, Germany) used as received. Water for injection purchased from Braun (Braun-Melsungen AG, Melsungen, Germany) for the production of the nanosuspensions. Demineralised water was filtered through Sartobran PH$_2$O membrane filters (Sartorius stedim biotech, Germany) and used for laser diffraction analysis.

Primary Packing Material

15R Vials from Lutz GmbH (Wertheim, Germany) and 20 mm West Flurotec® lyophilization stoppers from West Pharmaceutical Services, Inc. (Lionville, Pa., USA) were used as received. All vials were placed onto the shelf using a bottomless-tray.

Production of Nanosuspensions 100 mg/mL Itraconazole was mixed with either 50 mg/mL of Poloxamer 338 or 50 mg/mL of Cremophor EL and prepared by wet bead milling in a high shear-media mill (Netzsch MiniCer®). For milling, 0.3 mm yttrium stabilized zirconia beads were used. For data comparison purpose, 100 mg/mL Rilpivirine was stabilized with 50 mg/mL Poloxamer 338 and milled using the same procedure as mentioned above. The rilpivirne concentration was then further increased to 200 mg/mL and stabilized again with 50 mg/mL Poloxamer 338. The resulting stock-nanosuspensions were mixed with 50 mg/mL PVP K15, trehalose or sucrose.

Laser Diffraction Analysis

A Malvern MasterSizer® was used to allow a determination of the particle size distribution over a range in which even agglomerates can be found. Dependent on the steric stabilizer present in the formulation, an aqueous solution of 5 mg/mL Poloxamer 338 or Cremophor EL was used as a medium since particle stability was not sufficient in pure water during a measurement. Basis for particle size calculation was the Mie theory with a product refractive index of 1.65 and product absorption of 0.001. The obtained fitting curve achieved by the MasterSizer 2000 Software indicated validity of the optical model. Background and measurement integration time were kept at 60 seconds, measurements were conducted in triplicate (n=3) per unit sample.

Freeze-Drying Procedure 1 mL of each formulation was filled in 15R vials. Lyophilization was then performed on a laboratory scale freeze-dryer (VirTis Advantage Plus, SP Scientific, USA). Freezing was conducted at −40° C. (shelf inlet temperature) for 60 minutes including equilibrating steps at +5° C. and −5° C. for 15 minutes each. To facilitate crystallization of the Poloxamer 338 in the formulation, an annealing step at −20° C. (shelf inlet temperature) for 90 minutes was implemented. The shelf temperature ramp rates from the freezing set-point to the primary drying shelf temperature setting were 1° C./min throughout the study. The shelf inlet temperature set-point during primary and secondary drying was 40° C. The holding time (soak period) of this step was either 60 minutes or 600 minutes to allow a modulation in water content in the samples. The chamber pressure during primary and secondary drying was controlled at 100 mTorr throughout the experiments. Note that the freeze-drying cycles were performed in duplicate (n=2) per formulation.

Product temperatures during freeze-drying were measured using calibrated 30 gauge T-type copper/constantan thermocouples from Omega (Omega Engineering, Stamford, Conn.). Each thermocouple was introduced through a stopper and positioned bottom-center of the vial to obtain both a representative temperature monitoring in the product and an accurate endpoint detection of the ice sublimation phase.

Differential Scanning Calorimetry, DSC

Determination of thermal transitions in all formulation mixtures was performed using a MettlerDSC822e (Mettler Toledo, Greifensee, Switzerland). Data acquisition was performed in the temperature range between 5° C. and 150° C. The applied heating rate was 5° C./min.

Karl Fischer (KF) Residual Moisture Measurements

Residual moisture of the lyophilized samples was measured using a Metrohm Karl Fischer 831 KF Coulometer combined with a Metrohm Thermoprep 832 unit. About 50 mg of product was weighed into a custom glass vial and then inserted into the oven unit after purging the sample vial with dry nitrogen. The product was heated to 140° C. for a defined time period and the moisture was accumulated in the titration solvent. Dependent on the sample weight, residual moisture content was reported in percent (%).

Stability Testing Procedure

Directly after freeze-drying the products (n=4) were sealed and stored at 25° C. and 40° C./75RH, respectively. After 1, 2 and 3 months samples were analyzed in terms of mean particle size and particle size distribution. DSC and Karl-Fischer measurements were performed after freeze-drying as well as after 3 months of storage.

TABLE 1

$d^{50}$, $d^{95}$ and RDI-values obtained directly after completion of freeze-drying and after 3 months of storage at 25° C. and 40° C., respectively. Formulation: 200 mg/mL of rilpivirine nanoparticle concentration stabilized with 50 mg/mL Poloxamer 338 alone or in combination with 50 mg/mL Polyvinylpyrrolidone (PVP type K15), 50 mg/mL trehalose or 50 mg/mL sucrose. Note that the calculated standard deviations (n = 4) were small indicating very consistent $d^{50}$, $d^{95}$ and RDI-values. Abbreviations represent P338 = Poloxamer 338, Tr = Trehalose, Su = Sucrose, PVP = PVP K15, $T_0$ = $d^{50}$, $d^{95}$ and RDI-values determined directly after freeze-drying, $T_3$ = $d^{50}$, $d^{95}$ and RDI-value after 3 months of storage.

|  |  | $d^{50}$-value (μm) | $d^{95}$-value (μm) | RDI (%) |
|---|---|---|---|---|
| without protectant | $T_0$ | 0.185 | 1.18 | — |
|  | $T_3$ at 25° C. | 0.185 | 1.89 | 75% |
|  | $T_3$ at 40° C. | 0.199 | 3.01 | 42% |
| Tr | $T_0$ | 0.166 | 0.82 | — |
|  | $T_3$ at 25° C. | 0.168 | 0.85 | 98% |
|  | $T_3$ at 40° C. | 0.177 | 0.95 | 94% |
| Su | $T_0$ | 0.168 | 0.90 | — |
|  | $T_3$ at 25° C. | 0.172 | 0.94 | 96% |
|  | $T_3$ at 40° C. | 0.195 | 1.48 | 65% |
| PVP | $T_0$ | 0.165 | 0.80 | — |
|  | $T_3$ at 25° C. | 0.159 | 0.78 | 101% |
|  | $T_3$ at 40° C. | 0.161 | 0.85 | 98% |

Further data are shown in FIGS. 1 to 6.

Experimental Part 2 a) Drug Nanosuspensions with PVP K12 or PVPK17 or Trehalose

|  | Rilpivirine (mg/ml) | Poloxamer 338 (mg/ml) | PVP K12 (mg/ml) | PVP K17 (mg/ml) | Trehalose (mg/ml) |
|---|---|---|---|---|---|
| Drug nanosuspension 1 | 200 | 50 |  | 50 |  |
| Drug nanosuspension 2 | 200 | 50 |  | 25 |  |
| Drug nanosuspension 3 | 200 | 50 | 50 |  |  |
| Drug nanosuspension 4 | 200 | 50 | 25 |  |  |
| Drug nanosuspension 5 | 200 | 50 |  |  | 50 |
| Drug nanosuspension 5a | 200 | 50 |  | 25 | 25 |
| Drug nanosuspension 6 | 200 | 33.3 |  | 50 |  |
| Drug nanosuspension 7 | 300 | 50 |  | 50 |  |
| Drug nanosuspension 7a | 300 | 50 |  | 75 |  |

Preparation of Drug Nanosuspensions 1 to 5a
Preparation of Concentrated Nanosuspension:

112.5 g of Poloxamer 338 was dissolved in water for injection. 450 g of rilpivirine was added and suspended. Water for injection was added until the desired end weight (300 mg rilpivirine and 75 mg Poloxamer/ml). The resulting suspension was milled in a Netzsch Pharma Labstar (526 ml milling chamber) with 80% bead load of 300 μm yttrium stabilized zirconia beads. Milling was performed at agitator speed of 2000 rpm until the appropriate particle size was reached (measured on Malvern).

After Milling:

For drug nanosuspension 1, 133.3 ml (or 144 g) of the concentrated nanosuspension was taken and 50 ml of a 200 mg/ml PVP K17 stock solution was added. Water for injection was added until 200 ml (or 212.6 g) and the mixture was stirred until homogeneous.

For drug nanosuspension 2, 133.3 ml (or 144 g) of the concentrated nanosuspension was taken and 25 ml of a 200 mg/ml PVP K17 stock solution was added and the mixture was stirred until homogeneous. Water for injection was added until 200 ml (or 212.6 g) and the mixture was stirred until homogeneous.

For drug nanosuspension 3, 133.3 ml (or 144 g) of the concentrated nanosuspension was taken and 50 ml of a 200 mg/ml PVP K12 stock solution was added. Water for injection was added until 200 ml (or 212.6 g) and the mixture was stirred until homogeneous.

For drug nanosuspension 4, 133.3 ml (or 144 g) of the concentrated nanosuspension was taken and 25 ml of a 200 mg/ml PVP K12 stock solution was added. Water for injection was added until 200 ml (or 212.6 g) and the mixture was stirred until homogeneous.

For drug nanosuspension 5, 133.3 ml (or 144 g) of the concentrated nanosuspension was taken and 50 ml of a 200 mg/ml trehalose stock solution was added. Water for injection was added until 200 ml (or 212.6 g) and the mixture was stirred until homogeneous.

For drug nanosuspension 5a, 133.3 ml (or 144 g) of the concentrated nanosuspension was taken and 25 ml of a 200 mg/ml PVP K17 stock solution was added. 25 ml of a 200 mg/ml trehalose stock solution was added. Water for injection was added until 200 ml (or 212.6 g) and the mixture was stirred until homogeneous.

Preparation of Drug Nanosuspensions 6 and 7
Preparation of Nanosuspension 6:

16.65 g of Poloxamer 338 was dissolved in water for injection. 100 g of rilpivirine was added and suspended. Water for injection was added until the desired end weight. The resulting suspension was milled in a Netzsch Pharma Labstar (137 ml milling chamber) with 80% bead load of 300 μm yttrium stabilized zirconia beads. Milling was performed at agitator speed of 2000 rpm until the appropriate particle size was reached (measured on Malvern). 25 g of PVP K17 powder was added and stirred until dissolved.

Preparation of Nanosuspension 7:

25 g of Poloxamer 338 was dissolved in water for injection. 150 g of rilpivirine was added and suspended. Water for injection was added until the desired end weight. The resulting suspension was milled in a Netzsch Pharma Labstar (137 ml milling chamber) with 80% bead load of 300 μm yttrium stabilized zirconia beads. Milling was performed at agitator speed of 2000 rpm until the appropriate particle size was reached (measured on Malvern). To 215.92 ml of said suspension, 10.80 g of PVP K17 powder was added and stirred until dissolved.

Preparation of Nanosuspension 7a:

25 g of Poloxamer 338 was dissolved in water for injection. 150 g of rilpivirine was added and suspended. Water for injection was added until the desired end weight. The resulting suspension was milled in a Netzsch Pharma Labstar (137 ml milling chamber) with 80% bead load of 300 μm yttrium stabilized zirconia beads. Milling was performed at agitator speed of 2000 rpm until the appropriate particle size was reached (measured on Malvern). To 206.92 ml of said suspension, 15.52 g of PVP K17 powder was added and stirred until dissolved.

Drug Nanosuspensions 1 to 7a were Freeze Dried as Follows:

3 mL of each formulation (for drug nanosuspension 7 and 7a, 2 ml of fill volume was used) was filled in 8 ml lyo vials. Lyophilization was then performed on a HOF pilot plant freeze-dryer. Freeze drying cycle was conducted as follows: loading at 20° C.; freezing for 45 min at 5° C., 20 min at −5° C., 2 h40 min at −40° C., 2 h10 min at −20° C., 40 min at −40° C.; under vacuum (0.08 mbar), after 2 min period at −40° C., drying for 110 h21 min at 40° C. and 40 min further drying at 20° C. directly after freeze drying (T0) and after 2 weeks, 1 month, 3 months and 5 month storage at 40° C. are reported in Table 2. Reconstitution was done in water (up to and including 1 month stability) or 5% glucose water (3 and 5 month stability).

TABLE 2

| Formulation | Time point | d10 (μm) | d50 (μm) | d90 (μm) | d99 (μm) |
|---|---|---|---|---|---|
| 1: reconstituted to 200/50/50 PVPK17 | Before FD | 0.072 | 0.165 | 0.614 | 1.163 |
| | T0 after FD | 0.071 | 0.163 | 0.637 | 1.199 |
| | 2 weeks 40° C. | 0.074 | 0.179 | 0.701 | 1.412 |
| | 1 month 40° C. | 0.073 | 0.176 | 0.717 | 1.406 |
| | 3 month 40° C. | 0.073 | 0.175 | 0.688 | 1.284 |
| | 5 month 40° C. | 0.073 | 0.178 | 0.722 | 1.319 |
| 2: reconstituted to 200/50/25 PVPK17 | Before FD | 0.072 | 0.166 | 0.607 | 1.173 |
| | T0 after FD | 0.072 | 0.169 | 0.647 | 1.215 |
| | 2 weeks 40° C. | 0.073 | 0.175 | 0.682 | 1.253 |
| | 1 month 40° C. | 0.073 | 0.177 | 0.713 | 1.312 |
| | 3 month 40° C. | 0.073 | 0.175 | 0.707 | 1.310 |
| | 5 month 40° C. | 0.074 | 0.181 | 0.736 | 1.309 |
| 2: reconstituted to 300/75/37.5 | 2 weeks 40° C. | 0.074 | 0.183 | 0.700 | 1.227 |
| | 1 month 40° C. | 0.073 | 0.172 | 0.695 | 1.283 |
| 3: reconstituted to 200/50/50 PVPK12 | Before FD | 0.071 | 0.162 | 0.584 | 1.151 |
| | T0 after FD | 0.073 | 0.171 | 0.660 | 1.258 |
| | 2 weeks 40° C. | 0.073 | 0.176 | 0.713 | 1.346 |
| | 1 month 40° C. | 0.073 | 0.174 | 0.746 | 1.424 |
| | 3 month 40° C. | 0.073 | 0.176 | 0.743 | 4.414 |
| | 5 month 40° C. | 0.073 | 0.178 | 0.752 | 1.377 |
| 4: reconstituted to 200/50/25 PVPK12 | Before FD | 0.072 | 0.167 | 0.612 | 1.157 |
| | T0 after FD | 0.073 | 0.171 | 0.663 | 1.267 |
| | 2 weeks 40° C. | 0.074 | 0.181 | 0.740 | 1.429 |
| | 1 month 40° C. | 0.073 | 0.173 | 0.733 | 1.362 |
| | 3 month 40° C. | 0.072 | 0.172 | 0.732 | 1.408 |
| | 5 month 40° C. | 0.073 | 0.179 | 0.778 | 1.442 |
| 5: reconstituted to 200/50/50 Trehalose | Before FD | 0.072 | 0.166 | 0.604 | 1.151 |
| | T0 after FD | 0.073 | 0.171 | 0.667 | 1.239 |
| | 2 weeks 40° C. | 0.074 | 0.194 | 1.403 | 2.97 |
| 5a: reconstituted to 200/50/25 Trehalose/ 25 PVPK17 | Before FD | 0.071 | 0.161 | 0.595 | 1.162 |
| | T0 after FD | 0.072 | 0.169 | 0.650 | 1.221 |
| | 2 weeks 40° C. | 0.071 | 0.163 | 0.688 | 1.384 |
| | 1 month 40° C. | 0.073 | 0.176 | 0.786 | 1.549 |
| | 3 month 40° C. | 0.073 | 0.174 | 0.749 | 1.413 |
| | 5 month 40° C. | 0.073 | 0.178 | 0.780 | 1.448 |
| 6: reconstituted to 300/50/75 PVPK17 | Before FD | 0.071 | 0.159 | 0.589 | 1.308 |
| | T0 after FD | 0.072 | 0.163 | 0.657 | 1.549 |
| | 2 weeks 40° C. | 0.073 | 0.172 | 0.692 | 1.331 |
| | 1 month 40° C. | 0.070 | 0.161 | 0.700 | 1.765 |
| | 3 month 40° C. | 0.073 | 0.174 | 0.709 | 1.408 |
| | 5 month 40° C. | 0.073 | 0.179 | 0.764 | 1.440 |
| 7: reconstituted to 300/50/50 PVPK17 | Before FD | 0.072 | 0.164 | 0.633 | 1.239 |
| | T0 after FD | 0.073 | 0.173 | 0.759 | 2.492 |
| | 2 weeks 40° C. | 0.078 | 0.199 | 0.801 | 2.994 |
| | 3 month 40° C. | 0.073 | 0.177 | 0.818 | 2.095 |
| | 5 month 40° C. | 0.073 | 0.178 | 0.882 | 1.811 |
| 7a: reconstituted to 300/50/75 PVPK17 | Before FD | 0.072 | 0.168 | 0.635 | 1.183 |
| | T0 after FD | 0.072 | 0.166 | 0.747 | 2.803 |
| | 2 weeks 40° C. | 0.078 | 0.215 | 0.921 | 4.200 |
| | 3 month 40° C. | 0.073 | 0.176 | 0.769 | 1.563 |
| | 5 month 40° C. | 0.073 | 0.178 | 0.806 | 1.556 | b) Screening of Different Concentrations of PVPK17

|  | Rilpivirine (mg/ml) | Poloxamer 338 (mg/ml) | PVP K17 (mg/ml) |
| --- | --- | --- | --- |
| Drug nanosuspension 8 | 200 | 33.3 | 12.5 |
| Drug nanosuspension 9 | 200 | 33.3 | 25 |
| Drug nanosuspension 10 | 200 | 33.3 | 37.5 |
| Drug nanosuspension 11 | 200 | 33.3 | 50 |

Preparation of Drug Nanosuspensions 8 to 11
Preparation of Concentrated Nanosuspension:

50 g of Poloxamer 338 was dissolved in water for injection. 300 g of rilpivirine was added and suspended. Water for injection was added until the desired end weight (300 mg rilpivirine and 50 mg Poloxamer/ml). The resulting suspension was milled in a Netzsch Pharma Labstar (526 ml milling chamber) with 80% bead load of 300 μm yttrium stabilized zirconia beads. Milling was performed at agitator speed of 2000 rpm until the appropriate particle size was reached (measured on Malvern).

After Milling:

For drug nanosuspension 8, 65 ml (or 70.4 g) of the concentrated nanosuspension was taken and 6.1 ml of a 200 mg/ml PVP K17 stock solution was added and the mixture was stirred until homogeneous. Water for injection was added until end volume (97.5 ml) or end weight (103.6 g).

For drug nanosuspension 9, 65 ml (or 70.4 g) of the concentrated nanosuspension was taken and 12.2 ml of a 200 mg/ml PVP K17 stock solution was added and the mixture was stirred until homogeneous. Water for injection was added until end volume (97.5 ml) or end weight (103.6 g).

For drug nanosuspension 10, 65 ml (or 70.4 g) of the concentrated nanosuspension was taken and 18.3 ml of a 200 mg/ml PVP K17 stock solution was added and the mixture was stirred until homogeneous. Water for injection was added until end volume (97.5 ml) or end weight (103.6 g).

For drug nanosuspension 11, 65 ml (or 70.4 g) of the concentrated nanosuspension was taken and 24.4 ml of a 200 mg/ml PVP K17 stock solution was added and the mixture was stirred until homogeneous. Water for injection was added until end volume (97.5 ml) or end weight (103.6 g).

Drug Nanosuspensions 8 to 11 were Freeze Dried as Follows:

3 mL of each formulation was filled in 8 ml lyo vials. Lyophilization was then performed on a HOF pilot plant freeze-dryer. Freeze drying cycle was conducted as follows: loading at 20° C.; freezing for 45 min at 5° C., 20 min at −5° C., 2 h40 min at −50° C., 2 h10 min at −20° C., 40 min at −50° C.; under vacuum (0.08 mbar), after 2 min period at −50° C., drying for 42 h21 min at 40° C. and 40 min further drying at 20° C.

The $d^{10}$, $d^{50}$, $d^{90}$ and $d^{99}$ (μm) determined before freeze drying (FD) and determined directly after freeze drying (T0) and after 1 and 3 months storage at 40° C. are reported in Table 3.

The nanosuspensions were reconstituted in 5% glucose water to a corresponding concentration of 300 mg rilpivirine/ml.

TABLE 3

| Formulation | Time point | d10 (μm) | d50 (μm) | d90 (μm) | d99 (μm) |
| --- | --- | --- | --- | --- | --- |
| 8: reconstituted to 300/50/18.75 PVPK17 | Before FD | 0.071 | 0.160 | 0.503 | 1.003 |
|  | T0 after FD | 0.072 | 0.163 | 0.587 | 1.119 |
|  | 1 month 40° C. | 0.073 | 0.176 | 0.706 | 1.416 |
|  | 3 month 40° C. | 0.073 | 0.176 | 0.719 | 1.470 |
| 9: reconstituted to 300/50/37.5 PVPK17 | Before FD | 0.071 | 0.159 | 0.495 | 1.002 |
|  | T0 after FD | 0.072 | 0.163 | 0.583 | 1.106 |
|  | 1 month 40° C. | 0.072 | 0.166 | 0.629 | 1.188 |
|  | 3 month 40° C. | 0.072 | 0.171 | 0.662 | 1.211 |
| 10: reconstituted to 300/50/56.25 PVPK17 | Before FD | 0.071 | 0.158 | 0.482 | 0.974 |
|  | T0 after FD | 0.072 | 0.165 | 0.584 | 1.104 |
|  | 1 month 40° C. | 0.073 | 0.172 | 0.611 | 1.144 |
|  | 3 month 40° C. | 0.072 | 0.169 | 0.625 | 1.183 |
| 11: reconstituted to 300/50/75 PVPK17 | Before FD | 0.071 | 0.158 | 0.488 | 1.010 |
|  | T0 after FD | 0.072 | 0.165 | 0.579 | 1.104 |
|  | 1 month 40° C. | 0.073 | 0.171 | 0.613 | 1.195 |
|  | 3 month 40° C. | 0.073 | 0.170 | 0.626 | 1.185 | c) Screening of Different Tonifying Agents

|  | Rilpivirine (mg/ml) | Poloxamer 338 (mg/ml) | PVP K17 (mg/ml) | Glucose (mg/ml) | Citric acid (mg/ml) | NaCl (mg/ml) |
| --- | --- | --- | --- | --- | --- | --- |
| Drug nanosuspension 12 | 200 | 33.3 | 25 | 33.3 |  |  |
| Drug nanosuspension 13 | 200 | 33.3 | 25 | 23 |  | 5 |
| Drug nanosuspension 14 | 200 | 33.3 | 25 |  | 16 |  |
| Drug nanosuspension 15 | 200 | 33.3 | 25 |  |  | 6 |

Preparation of Drug Nanosuspensions 12 to 15
Preparation of Concentrated Nanosuspension:

50 g of Poloxamer 338 was dissolved in water for injection. 300 g of rilpivirine was added and suspended. Water for injection was added until the desired end weight (300 mg rilpivirine and 50 mg Poloxamer/ml). The resulting suspension was milled in a Netzsch Pharma Labstar (526 ml milling chamber) with 80% bead load of 300 μm yttrium stabilized zirconia beads. Milling was performed at agitator speed of 2000 rpm until the appropriate particle size was reached (measured on Malvern).

After Milling:

For drug nanosuspension 12, 65 ml (or 70.4 g) of the concentrated nanosuspension was taken and 12.2 ml of a 200 mg/ml PVP K17 stock solution was added and the mixture was stirred until homogeneous. 16.3 ml of a 200 mg/ml glucose stock solution (220 mg/ml of glucose monohydrate)

was added and the mixture was stirred until homogeneous. Water for injection was added until end volume (97.5 ml) or end weight (103.6 g).

For drug nanosuspension 13, 65 ml (or 70.4 g) of the concentrated nanosuspension was taken and 12.2 ml of a 200 mg/ml PVP K17 stock solution was added and the mixture was stirred until homogeneous. 11.2 ml of a 200 mg/ml glucose stock solution (220 mg/ml of glucose monohydrate) was added and the mixture was stirred until homogeneous. 1.6 ml of a 300 mg/ml citric acid stock solution pH 5.5 was added and the mixture was stirred until homogeneous. NaOH solution was added until pH 6. Water for injection was added until end volume (97.5 ml) or end weight (103.6 g).

For drug nanosuspension 14, 65 ml (or 70.4 g) of the concentrated nanosuspension was taken and 12.2 ml of a 200 mg/ml PVP K17 stock solution was added and the mixture was stirred until homogeneous. 5.2 ml of a 300 mg/ml citric acid stock solution pH 5.5 was added and the mixture was stirred until homogeneous. NaOH solution was added until pH 6. Water for injection was added until end volume (97.5 ml) or end weight (103.6 g).

For drug nanosuspension 15, 65 ml (or 70.4 g) of the concentrated nanosuspension was taken and 12.2 ml of a 200 mg/ml PVP K17 stock solution was added and the mixture was stirred until homogeneous. 5.9 ml of a 100 mg/ml NaCl stock solution was added and the mixture was stirred until homogeneous. Water for injection was added until end volume (97.5 ml) or end weight (103.6 g).

Drug Nanosuspensions 12 to 15 were Freeze Dried as Follows:

3 mL of each formulation was filled in 8 ml lyo vials. Lyophilization was then performed on a HOF pilot plant freeze-dryer. Freeze drying cycle was conducted as follows: loading at 20° C.; freezing for 45 min at 5° C., 20 min at −5° C., 2 h40 min at −50° C., 2 h10 min at −20° C., 40 min at −50° C.; under vacuum (0.08 mbar), after 2 min period at −50° C., drying for 42 h21 min at 40° C. and 40 min further drying at 20° C.

The $d^{10}$, $d^{50}$, $d^{90}$ and $d^{99}$ (μm) determined before freeze drying (FD) and determined directly after freeze drying (T0) and after 1 and 3 months storage at 40° C. are reported in Table 4.

The nanosuspensions were reconstituted in water to a corresponding concentration of 300 mg rilpivirine/ml. (hypertonic).

TABLE 4

| Formulation | Time point | d10 (μm) | d50 (μm) | d90 (μm) | d99 (μm) |
| --- | --- | --- | --- | --- | --- |
| 12: reconstituted to 300/50/37.5 PVP K17/50 Glucose | Before FD | 0.071 | 0.157 | 0.469 | 0.952 |
| | T0 after FD | 0.072 | 0.166 | 0.577 | 1.127 |
| | 1 month 40° C. | 0.073 | 0.176 | 0.722 | 1.338 |
| | 3 month 40° C. | 0.074 | 0.180 | 0.811 | 1.658 |
| 13: reconstituted to 300/50/37.5 PVP | Before FD | 0.071 | 0.157 | 0.459 | 0.949 |
| | T0 after FD | 0.072 | 0.167 | 0.595 | 1.128 |

TABLE 4-continued

| Formulation | Time point | d10 (μm) | d50 (μm) | d90 (μm) | d99 (μm) |
| --- | --- | --- | --- | --- | --- |
| K17/34.5Glucose/7.5 Citric acid | 1 month 40° C. | 0.073 | 0.177 | 0.757 | 1.605 |
| | 3 month 40° C. | 0.073 | 0.176 | 0.705 | 1.392 |
| 14: reconstituted to 300/50/37.5 PVP K17/24 Citric acid | Before FD | 0.071 | 0.157 | 0.459 | 0.949 |
| | T0 after FD | 0.072 | 0.167 | 0.595 | 1.110 |
| | 1 month 40° C. | 0.073 | 0.173 | 0.816 | 2.609 |
| | 3 month 40° C. | 0.074 | 0.185 | 1.225 | 3.848 |
| 15: reconstituted to 300/50/37.5 PVP K17/9 NaCl | Before FD | 0.071 | 0.158 | 0.476 | 0.975 |
| | T0 after FD | 0.073 | 0.172 | 0.602 | 1.129 |
| | 1 month 40° C. | 0.073 | 0.177 | 0.782 | 4.298 |
| | 3 month 40° C. | 0.072 | 0.171 | 0.708 | 1.565 |

The invention claimed is:

1. A freeze-dried nanosuspension comprising
   4-[[4-[[4-(2-cyanoethenyl)-2,6-dimethylphenyl]amino]-2-pyrimidinyl]amino]benzonitrile or a stereoisomeric form thereof; or a pharmaceutically acceptable salt thereof,
   a steric stabilizer which is a solid at room temperature and which is a poloxamer, and
   polyvinyl pyrrolidone;
   wherein the freeze dried nanosuspension has a re-dispersibility index of at least 90% after storage for 3 months at 25° C.

2. The freeze-dried nanosuspension as claimed in claim 1 wherein the poloxamer is poloxamer 338.

3. The freeze-dried nanosuspension as claimed in claim 1 wherein the drug is 4-[[4-[[4-(2-cyanoethenyl)-2,6-dimethylphenyl]amino]-2-pyrimidinyl]-amino]benzonitrile base.

4. The freeze-dried nanosuspension as claimed claim 3 wherein the drug is E-4-[[4-[[4-(2-cyanoethenyl)-2,6-dimethylphenyl]amino]-2-pyrimidinyl]-amino]benzonitrile.

5. A process for preparing an aqueous nanosuspension comprising reconstituting the freeze-dried nanosuspension according to claim 1 with an aqueous dispersion medium.

6. The freeze-dried nanosuspension of claim 1, having a re-dispersibility index of at least 92% after storage for 3 months at 25° C.

7. The freeze-dried nanosuspension of claim 1, having a re-dispersibility index of at least 94% after storage for 3 months at 25° C.

8. The freeze-dried nanosuspension of claim 1, having a re-dispersibility index of at least 96% after storage for 3 months at 25° C.

9. The freeze-dried nanosuspension of claim 1, having a re-dispersibility index of at least 98% after storage for 3 months at 25° C.

10. An aqueous nanosuspension prepared according to the method of claim 5.

11. A method of treating HIV infection in a subject comprising
    reconstituting the freeze-dried nanosuspension of claim 1 with a pharmaceutically acceptable aqueous dispersion medium to form an aqueous nanosuspension; and
    administering the aqueous nanosuspension to the subject.

* * * * *